United States Patent
Iannotti et al.

(10) Patent No.: US 6,326,042 B1
(45) Date of Patent: *Dec. 4, 2001

(54) ANTIMICROBIAL USE OF HEAT-TREATED LACTIC AND/OR GLYCOLIC ACID COMPOSITIONS FOR TREATMENT OF GROUND MEATS

(75) Inventors: Eugene L. Iannotti; Richard E. Mueller, both of Columbia, MO (US); Zhonglin Jin, Columbus, OH (US); Nan Unklesbay, Columbia, MO (US); Ann Allanson, Evanston, IL (US)

(73) Assignee: The Curators of the University of Missouri, Columbia, MO (US)

( * ) Notice: Subject to any disclaimer, the term of this patent is extended or adjusted under 35 U.S.C. 154(b) by 159 days.

This patent is subject to a terminal disclaimer.

(21) Appl. No.: 09/304,878

(22) Filed: May 4, 1999

Related U.S. Application Data

(63) Continuation-in-part of application No. 08/863,347, filed on May 29, 1997, now Pat. No. 5,900,266.

(51) Int. Cl.$^7$ .................................................. A23L 1/317
(52) U.S. Cl. .......................... 426/332; 426/335; 426/532; 426/626; 426/650
(58) Field of Search .................................. 426/332, 335, 426/532, 626, 650

(56) References Cited

U.S. PATENT DOCUMENTS

| | | | |
|---|---|---|---|
| Re. 35,320 | 8/1996 | Kinnersley et al. | 504/161 |
| 4,158,706 | * 6/1979 | Ernst et al. | 426/332 |
| 4,267,198 | * 5/1981 | Sato et al. | 426/332 |
| 4,801,739 | 1/1989 | Franz et al. | 560/185 |
| 5,093,140 | 3/1992 | Watanabe | 426/326 |
| 5,178,890 | 1/1993 | van den Niewelaar et al. | 426/332 |
| 5,238,841 | 8/1993 | Kinnersley et al. | 435/240.54 |
| 5,274,127 | 12/1993 | Sinclair et al. | 549/274 |
| 5,357,034 | 10/1994 | Fridman et al. | 528/354 |
| 5,434,241 | 7/1995 | Kim et al. | 528/354 |
| 5,900,266 | * 5/1999 | Iannotti et al. | 426/332 |

OTHER PUBLICATIONS

Anderson, M.E. and Marshall, R.T. [1989], "Interaction of concentration and temperature of acetic acid solution on reduction of various species of microorganisms on beef surface," Journal of Food Protection 52(5):312–315.

Barakat, I. et al. (1996) "Macromolecular Engineering of Polylactones and Polyactides. XXI. Controlled Synthesis of Low Molecular Weight Polyactide Macromonomers," J. Polym. Sci. Part A: Polym. Chem. 34:497–502.

Conn, R.E., et al. (1995), "Safety assessment of polylactide (PLA) for use as a food–contact polymer," Food and Chemical Toxicology 33(4)273–283.

(List continued on next page.)

Primary Examiner—Helen Pratt
(74) Attorney, Agent, or Firm—Greenlee, Winner and Sullivan, P.C.

(57) ABSTRACT

Heat-treated lactic and/or glycolic acid compositions are provided herein which are useful for antimicrobial treatment of surfaces, preferably food surfaces including fruits, vegetables and animal carcasses and of particulate materials, preferably ground meats, or other materials into which the compositions may be mixed. The heat-treated lactic and/or glycolic acid compositions have an average molecular weight preferably less than or equal to about 700 D and are mixtures of single molecules of the acid and ester complexes of the acid molecules containing two to no more than about ten molecules per complex. Preferably, these compositions comprise more than about 50 weight percent of the ester complexes, and more preferably about 75 weight percent. Aqueous solutions of these compositions and methods for making and using the compositions are also provided, as are food materials comprising such compositions.

22 Claims, 11 Drawing Sheets

OTHER PUBLICATIONS

Filachione, E.M. and Fisher, C.H. (1994), "Lactic Acid Condensation Polymers, Preparation by Batch and Continous Methods," Ind. and Eng. Chemistry 36:223–228.

Fukuzaki, H. et al. (1989) "Synthesis of Copoly(D,L–Lactic Acid) with Relatively Low Molecular Weight And In Vitro Degradation," Eur. Polym. J. 25(10):1019–1026.

Gill, C.O. and Penney, N. [1985], "Modification of in–pack conditions to extend the storage life of vacuum packed lamb," Meat Science 14:43–60.

Grau, F.H. (1986), "Microbial Ecology of Meat and Poultry," Advances in Meat Research, vol. 2, pp. 1–47.

Holten, C.H., (1971), "Stability of Crystalline L–(+)–Lactic Acid" in Lactic Acid, Properties and Chemistry of Lactic Acid and Derivatives, Stichting ILRA, Copenhagen K, Denmark.

Lockwood, L.B. et al., (1965) "Lactic Acid" Annals of NY Academy of Sciences, 119(3):854–867.

Smulders, F.J.M. and Kortenknie, F. [1985], "Control of the bacteriological condition of calf brain. II. Effect of lactic acid decontamination and frozen storage," Int. J. Food Microbiol. 2:293–299.

Smulders, F.J.M. and Woolthuis, C.H.J. [1983], "The immediate and delayed microbiological effects of lactic acid decontamination of calf carcasses. The influence on conventionally boned versus hot boned and vacuum packaged cuts," J. of Food Protection 48:838–847.

Smulders, F.J.M. and Woolthuis, C.H.J. [1983], "Influence of two levels of hygiene on the microbiological condition of veal as a product of two slaughtering/processing sequences," J. of Food Protection 46:1032–1035.

Snijders, J.M.A. et al. [1979], "Dekontamination schlachtwarmer Rinderkorper mit organishen Sauren," Fleischwirtschaft 59:656–663.

Van Netten, P. et al. [1984], "A note on catalase–enhanced recovery of acid injured cells of gram negative bacteria and its consequences for the assessment of the lethality of L–lactic acid decontamination of raw meat surfaces," J. Applied Bacteriology 57:169–173.

Woolthuis, C.H.J. and Smulders, F.J.M. (1985), "Microbial Decontamination of Calf Carcasses by Lactic Acid Sprays," J. Food Protection 48(10)832–837.

* cited by examiner

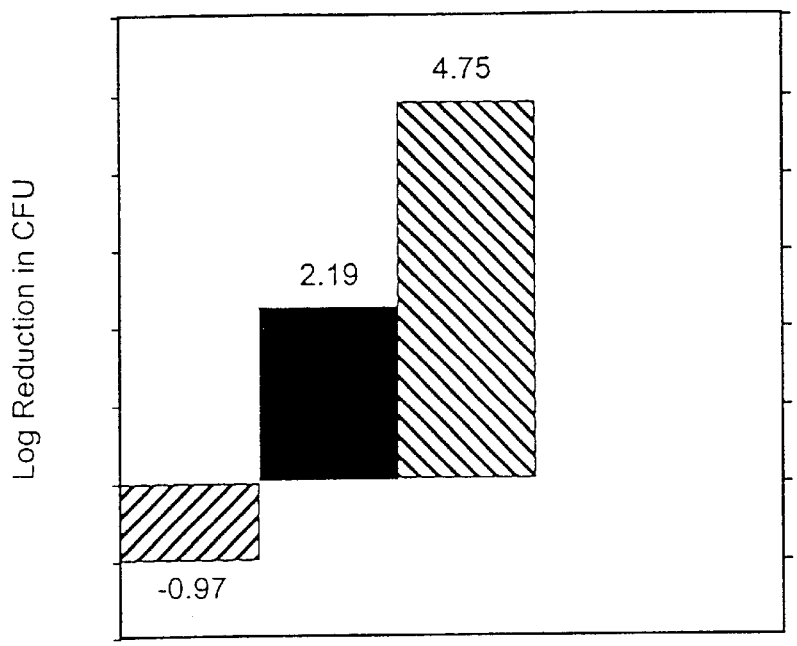
|////| Untreated Control  FIG. 1
▪ Water
|\\\\| 2.5% Heat-treated Lactic Acid
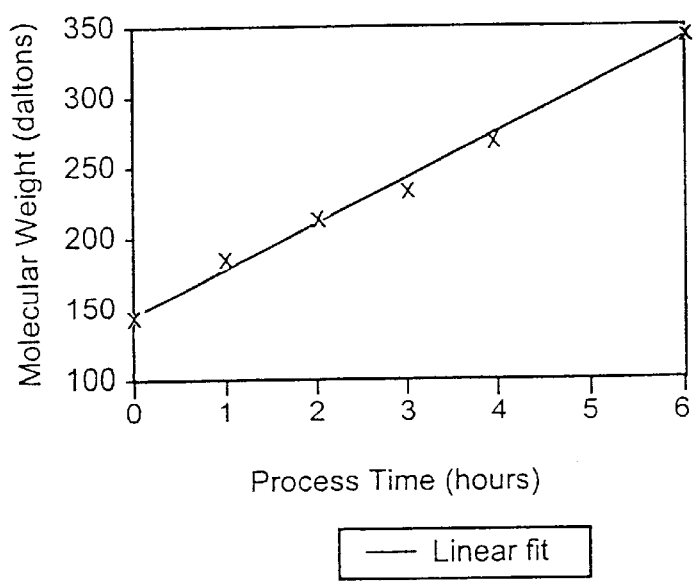
FIG. 2

ANTIMICROBIAL USE OF HEAT-TREATED LACTIC AND/OR GLYCOLIC ACID COMPOSITIONS FOR TREATMENT OF GROUND MEATS

This application is a continuation-in-part of U.S. application Ser. No. 08/863,347 filed May 29, 1997, now U.S. Pat. No. 5,900,266 issued May 4, 1999.

BACKGROUND OF THE INVENTION

Trends toward shorter cooking times, consumer demand for safety, and willingness to use litigation are increasing the pressure on the food industry to reduce risks in the food chain. Meats are of particular concern because they are easily contaminated with microorganisms and are an ideal environment for growth of bacteria. Pathogens such as Salmonella, Campylobacter, Listeria, Clostridium, *Escherichia coli* O157:H7, and the like can be present. Salmonella and *Campylobacter jejuni* are the leading causes of bacterial diarrhea. Listeria ingestion results in a high mortality rate. *Escherichia coli* O157:H7 is also particularly severe and the number of incidences are increasing.

In late 1992 and early 1993, a very large outbreak of *E. coli* O157:H7 infections occurred in Washington and several other western states. More than 500 confirmed infections in four states occurred, with 51 cases of emolytic uremic syndrome (HUS), and four deaths. This outbreak, traced to undercooked hamburgers served at multiple outlets of the same fast food chain (Centers for Disease Control and Prevention [1993] Update: Multistate Outbreak of *Escherichia coli* O157:H7 Infections from Hamburgers—Western United States, 1992–1993, Morbidity Mortality Weekly Report, 42:258–263) placed food safety, and *E. coli* O157:H7 in particular, into public, industrial, and regulatory prominence. With increased recognition of *E. coli* O157:H7 infections has come the investigation of increasing numbers of outbreaks, leading to the recognition of many "new" vehicles, including some foods not traditionally associated with enteric infections, such as dry-cured salami and lettuce (Tarr, P. I. et al., [1997], "Verotoxigenic *Escherichia coli* infection: U.S. overview," *J. Food Protection* 60:1466–1471) indicating this organism is particularly hardy. The number of outbreaks of *E. coli* O157:H7 infections reported to the Centers for Disease Control and Prevention (CDC) has increased in recent years. The Food and Drug Administration (FDA) approximates 25,000 cases of foodborne illness can be attributed to *E. coli* O157:H7 infections each year with as many as 100 deaths (FDA, [1997], "Food safety from farm to table: a national food safety initiative," Report to the President, Washington, D.C.). In 1989, the annual cost of *E. coli* infections was estimated at $223 million (Todd, E. C. D. [1989] "Preliminary estimates of costs of foodborne disease in the United States, *J. Food Protection* 52:595–601).

Analysis of foods associated with outbreaks of *E. coli* O157:H7 reveals that the infective dose is low. For example, 0.3 to 0.4 *E. coli* O157:H7 cells per g were detected in several intact packages of salami that were associated with a foodborne outbreak (Centers for Disease Control and Prevention [1995], "Surveillance for outbreaks of *Escherichia coli* O157:H7 infections-preliminary summary '94, Surveillance Summary No. SS-5"). This suggests that the infectious dose is quite low, less than a few hundred cells. Additional evidence for a low infectious dose is the capability for person-to-person transmission of *E. coli* O157:H7 infection. The serious nature of the disease combined with its apparent low infectious dose (<100 cells) qualify *E. coli* O157:H7 to be among the most serious of known foodborne pathogens.

Enteric bacterial pathogens must survive the acidity of the stomach before they reach the intestine and cause illness. Inoculation studies revealed that *E. coli* O157:H7 can survive fermentation, drying, and storage of fermented sausage for up to two months with only ca. 2 $\log_{10}$ decrease (Glass, K. A. et al., [1992] "Fate of *Escherichia coli* O157:H7 as affected by pH or sodium chloride and in fermented, dry sausage," Applied and *Environmental Microbiology*, 58:2513–2516). In 1991, an outbreak of serotype O157:H7 that infected 23 persons was traced to the consumption of fresh-pressed apple cider (Besser, R. E. et al., "An outbreak of diarrhea and hemolytic uremic syndrome from *Escherichia coli* O157:H7 in fresh-pressed apple cider," [1993] *J. Am. Med. Asso.* 269:2217–2220). The implicated cider had a pH value of 3.7 to 3.9 and contained no preservatives. The ability of *E. coli* O157:H7 to tolerate acidity was substantiated in 1993 when mayonnaise was implicated in a series of restaurant outbreaks that infected at least 48 people (Weagant, S. D. et al., [1994], "Survival of *Escherichia coli* O157:H7 in mayonnaise and mayonnaise-based sauces at room and refrigerated temperatures," *J. Food Protection* 57:629–631). Hot sprays of acetic, citric, and lactic acids at concentrations up to 1.5% did not have an inhibitory effect on *E. coli* O157:H7 in raw beef (Brackett, R. E. et al., [1994] "Ineffectiveness of hot acid sprays to decontaminate *Escherichia coli* O157:H7 on beef," *J. Food Protection* 57:198–203). The mechanism of acid tolerance of serotype O157:H7 has not been fully explained, but it appears to be due to the presence of proteins that can be induced by pre-exposing the bacteria to acidic conditions.

The primary source of O157:H7 infection is through beef products, most commonly undercooked ground beef (Boyce, T. G. et al. [1995] "Current Concepts: *Escherichia coli* O157:H7 and the hemolytic uremic syndrome," *The New Eng. J. Med.* 333:364–368).

Today's systems to control pathogenic bacteria still result in periodic food safety problems. Only continued analysis and control (Hazard Analysis Critical Control Point [HACCP]) as implemented by the Food and Drug Administration) and a multifaceted approach will allow a reasonable risk. The Food Safety and Inspection Service (FSIS)-approved antimicrobial treatments include hot water, steam and organic acids, such as lactic acid (up to 2.5%).

The use of organic acids, such as lactic acid, for decontamination of carcasses has been extensively studied because they reduce bacterial counts and are safe. The drawbacks of organic acid sprays is that high concentrations of the acids should not be used because of loss of sensory quality. Discoloration and the threshold for tasting the acid begins at about two percent.

Lactic acid has been used as an antimicrobial agent for treating animal carcasses. See U.S. Pat. No. 5,178,890, issued Jan. 12, 1993 to van den Niewelaar et al. for "Method for Improving the Bacteriological Quality of Slaughtered Poultry"; Grau, F. H. (1986), "Microbial Ecology of Meat and Poultry," *Advances in Meat Research*, 2:1–47; and U.S. Pat. No. 5,093,140 issued Mar. 3, 1992 to Watanabe for "Aqueous Bactericide for Animal Treatment." Application of lactic acid to meats causes a pH drop which results in death and sublethal injury to microorganisms (Anderson, M. E. and Marshall, R. T. [1989], "Interaction of concentration and temperature of acetic acid solution on reduction of various species of microorganisms on beef surface," *J. Food*

Protection 52(5):312–315). The pH remains low for a relatively short time because of the natural buffering in meat as discussed above. After spraying of hot calf carcasses with 1.25% (v/v) lactic acid, a surface pH fall of more than three units has been found. However, after 72 hours the pH had returned to its initial value. Repeating a lactic acid treatment of broiler carcasses neither decreased the surface pH further nor enhanced the bacteriostatic and bactericidal effects. See Woolthuis, C. H. J. and Smulders, F. J. M. (1985), "Microbial Decontamination of Calf Carcasses by Lactic Acid Sprays," *J. Food Protection* 48(10)832–837;

At high levels of initial contamination acceptable concentrations of lactic acid may not effect marked microbial lethality as theorized by Baird-Parker (Baird-Parker, A. C. [1980] "Organic Acids," in *Microbial Ecology of Foods. I Factors affecting life and death ofmicroorganismzs*," J. H. Silliker et al. (eds.), Academic Press, New York, pp. 126–135). When the initial contamination was low, the lethality effect of lactic acid on aerobic colony counts, though significant, did not exceed two or exceptionally three logo cycles. (See: Snijders, J. M. A. et al. [1979], "Dekontamination schlachtwarmer Rinderkorper mit organishen Sauren," *Fleischwirtschaft* 59:656–663; Smulders, F. J. M. and Woolthuis, C. H. J. [1983], "Influence of two levels of hygiene on the microbiological condition of veal as a product of two slaughtering/processing sequences," *J. Food Protection* 46:1032–1035; Smulders, F. J. M. and Woolthuis, C. H. J. [1983], "The immediate and delayed microbiological effects of lactic acid decontamination of calf carcasses. The influence on conventionally boned versus hot boned and vacuum packaged cuts," *J. Food Protection* 48:838–847; Smulders, F. J. M. and Kortenkiiie, F. [1985], "Control of the bacteriological condition of calf brain. II. Effect of lactic acid decontamination and frozen storage," *Int. J. Food Microbiol.* 2:293–299; Van Netten, P. et al. [1984], "A note on catalase-enhanced recovery of acid injured cells of gram negative bacteria and its consequences for the assessment of the lethality of L-lactic acid decontamination of raw meat surfaces," *J. Applied Bacteriology* 57:169–173; Gill, C. O. and Penney, N. [1985], "Modification of in-pack conditions to extend the storage life of vacuum packed lamb," *Meat Science* 14:43–60.) However, after storage of lactic acid-treated meat surfaces a so-called delayed bacteriostatic effect was found (Smulders and Woolthuis [1985], supra). It has also been found that lamb cuts treated with 5% lactic acid and vacuum packaged in foil laminate remained unspoiled for 12 weeks of chilled storage (Gill and Penney [1985] sapra).

Lactic acid is a natural metabolite of mammalian muscle tissue and has been generally recognized as safe (GRAS) by the FDA for human consumption. Sprays at less than or equal to 2.5 percent (by weight lactic acid have been approved for antimicrobial treatment of carcasses. High molecular weight polymers of lactic acid (polylactic acid) can be formed into food packaging materials. These materials biodegrade to form lactic acid, and their use for packaging of foods has also been generally recognized as safe by the FDA. See, e.g. Conn, R. E. et al. (1995), "Safety assessment of polylactide (PLA) for use as a food-contact polymer," *Food and Chemical Toxicology* 33(4)273–283.

Polylactic acid has been used for a number of purposes including biodegradable implants for wound healing, timed release vehicles for drugs, fertilizers and the like, films, and grocery bags. These usages generally specify high molecular weight (e.g. above about 8,000 D) polymers.

Polylactic acid up to a molecular weight of about 15,000 D is produced by heating and condensation of lactic acid. Depending on their molecular weight, these materials can be gel-like or resinous products. Low molecular weight lactic acid materials having molecular weights up to about 15,000 daltons (D) can be prepared by condensing free (monomeric) lactic acid with or without catalysts. Classic polymerization of lactic acid to high molecular weight polymers (above about 15,000 M.W.) is a three-step process: 1) polycondensation to low molecular weight material; 2) depolymerization and cyclic dimerization to lactide; and 3) repolymerization of the lactide to high molecular weight polylactic acid (PLA) by a ring-opening reaction.

U.S. Pat. No. 5,357,034 issued Oct. 18, 1994 to Fridman et al. entitled "Lactide Polymerization" teaches making a polylactic acid composition with molecular weight between 300 and 500 by heating 85–90 weight percent lactic acid in aqueous solution to 115° C. to 125° C. to remove water, and then further heating to 170° C. to 175° C. to form the polylactic acid over a period of 5 to 8 hours. This material was then further polymerized to form high molecular weight polylactides.

U.S. Pat. No. Re. 35320 issued Aug. 27, 1996 to Kinnersley et al. for "Method for Regulating Plant Growth" and divisional patent thereof, U.S. Pat. No. 5,238,841, discloses heating lactic acid to 100° C. under vacuum for 2½ hours to form oligomers of lactic acid having up to six molecules. Such compositions having up to six molecules were also formed by heating the dimer of L-lactic acid under reduced pressure. The dimer was obtained by hydrolysis of L-lactide. The compositions are used in aqueous solutions of 1–1000 ppm.

U.S. Pat. No. 5,274,127 issued Dec. 28,1993 to Sinclair et al. for "Lactide Production from Dehydration of Aqueous Lactic Acid Feed" teaches removal of water from lactic acid (88%) by heating at 120° C. to 185° C. under nitrogen bubbling. At various (unspecified) times, aliquots were removed and analyzed, and included oligomers of up to four molecules as well as lactide. At 150° C. (90 torr), the composition contained 27.8 weight percent monomers, 27.8 weight percent dimers, 20.2 weight percent trimers, 10.3 weight percent tetramers and 8.6 weight percent lactide. The object of this process was to maximize lactide production.

U.S. Pat. No. 4,801,739 issued Jan. 31, 1989 to Franz et al. for "Oligomeric Hydroxycarboxylic Acid Derivatives, Their Production and Use," discloses distilling lactic acid under argon atmosphere to 160° (presumably degrees C) for varying periods of time up to eight hours, to produce product having 12 or more lactic acid units.

None of the foregoing references teach useful heat-treated lactic acid compositions having average molecular weights less than about 700 D, and consisting of a mixture of lactic acid molecules and ester complexes of lactic acid molecules containing two to no more than about ten molecules per complex. Nor do these references teach dilute aqueous solutions having concentrations less than about 10 weight percent of the heat-treated lactic acid. Nor do any of the foregoing references teach uses of such compositions, particularly uses of such compositions as antimicrobial agents for cleaning surfaces such as meat carcasses.

SUMMARY OF THE INVENTION

Heat-treated lactic acid and/or glycolic acid compositions are provided herein which are useful for antimicrobial treatment of surfaces, preferably food surfaces including fruits, vegetables and animal carcasses, and of foods such as particulate foods like ground meats, into which the heat-treated acid materials can be mixed. Heat-treated lactic acid compositions have an average molecular weight less than or equal to about 700 D, and are mixtures of lactic acid molecules and ester complexes of lactic acid molecules containing two to no more than about ten molecules per complex. Preferably, these compositions comprise more than about 50 weight percent of the ester complexes and more preferably about 75 weight method of claim 1 wherein said heat-treated lactic or glycolic acid is added to said particulate material in an amount sufficient to maintain the pH thereof at less than about 5.0 after about seven days. percent. Preferably the compositions contain minimal amounts of lactide molecules, e.g., less than about 8.6 weight percent.

Lactic acid has the structural formula:

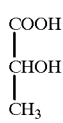

I and, unless otherwise specified, is an entiomeric mixture of D-lactic acid:

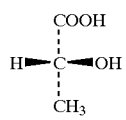

II and L-Lactic acid:

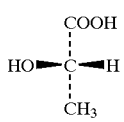

III

Lactic acid is water soluble, and can be dehydrated to form esters comprising two or more molecules:

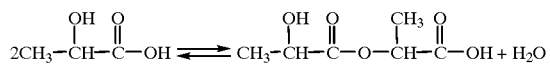

IV

This condensation reaction can be repeated to form esters containing higher numbers of lactic acid monomers, these products existing in equilibrium with each other. Removal of water shifts the equilibria to the right, favoring formation of larger complexes of lactic acid monomers joined by ester linkages.

The term lactic acid (LA), unless otherwise specified, means lactic acid such as commercially available lactic acid which has not been specially treated to form esterified complexes.

Glycolic acid is an analog of lactic acid in which the methyl group is replaced by a hydrogen substituent. Its behavior is similar to that of lactic acid and it may be substituted for lactic acid for purposes of this invention.

Formation of esterified complexes of lactic acid or glycolic acid monomers is accelerated by removal of water. The limitation to removal is the increasing viscosity in the reaction medium. The average molecular weight of the material is linearly related to polymerization time and temperature, although at higher temperatures breakdown of the complexes into lower molecular weight complexes and lactic acid monomers begins to occur. Thus the condensation reaction becomes self-limiting at about 15,000 MW. The final molecular weight is repeatable and predictable from run to run if the temperature, time, vacuum, and initial concentration of lactic acid are controlled.

The compositions of this invention are made by heating lactic acid solutions to drive off water and form complexes containing up to ten lactic acid molecules linked together via ester linkages. Preferably a concentrated lactic acid solution (e.g., about 85 weight percent or more) is heated at about 120° C. for about three hours. Vacuum pressures, e.g., about 4 mm Hg or less, are also preferably used. The compositions contain a mixture of such complexes containing two to ten molecules. The compositions are substantially free of complexes containing more than ten molecules per complex. Catalysts and other process conditions, e.g., as taught in U.S. Pat. No. 5,274,127, which promote formation of lactide rings should not be used in this process.

The heat-treated lactic acid compositions of this invention are used for reducing microbial contamination of surfaces such as surfaces of animal carcasses intended for food use. Pathogens which are reduced by the surface treatment methods of this invention include Salmonella spp., *Yersinia entercolitica*, enterpathogenic *E. coli* such as *E. coli* O157:H7, *Campylobacter jejuni*, and mesophilic Enterobacteriaceae.

The heat-treated lactic acid compositions of this invention are also useful for reducing bacterial contamination of particulate materials such as ground meats including ground beef, ground pork and sausage, or liquid or semisolid food materials into which the heat treated lactic acid materials may be mixed. Mixed into such materials in effective amounts, e.g., amounts sufficient to maintain the pH of the materials below about 5.0 and preferably below about 4.0 for about three to about seven days, these heat-treated lactic acid materials significantly inhibit bacterial growth. In particular, *E. coli* O157:H7, a pathogen which grows at low pH and is extremely toxic to humans, is inhibited by heat-treated lactic acid. Preferably the heat-treated lactic acid is added to such materials in aqueous solution of about 2% (w/w) at concentrations of between about 25 and about 30 mL/kilogram of particulate material, with thorough mixing.

Aqueous solutions containing between about 0.1 and about 10 weight percent, preferably less than or equal to about 2.5 weight percent, and more preferably less than or equal to about 2.0 weight percent, e.g., about 1.0 weight percent, of the above-described compositions comprising lactic acid and lactic acid complexes may be applied to the surface to be treated by spraying, painting, immersion of the surface, or other means known to the art to reduce the microbial population of such surfaces, or may be mixed into the food material being treated. These treatments provide reduction of microbes improved at least double, and generally orders of magnitude better than treatment with lactic acid alone, and in addition provide longer-lasting reduction of microbes in or on the treated materials.

Food materials treated with the compositions of this invention are also provided herewith. The term "food" includes any substance capable of supporting growth of microorganisms susceptible to inhibition by the methods of this invention. Preferably such food materials are particulate materials such as ground meats.

Glycolic acid, or mixtures of lactic and glycolic acid in any proportion, may be substituted for lactic acid in this invention.

BRIEF DESCRIPTION OF THE FIGURES

FIG. 1 is a graph showing Log Reduction in colony forming cells (CFU) of coliforms added to beef plate meat in a pilot scale test of this invention after spraying at 300 psi at room temperature with 2.5 weight percent heat-treated lactic acid of this invention (stippled bar), compared with the same treatment using water (dark grey bar) and untreated meat (bar with horizontal lines).

FIG. 2 is a graph showing the linear relationship between molecular weight of the heat-treated lactic acid product of this invention and processing time at 4 mm Hg and 120° C.

FIG. 6A shows pH at a storage temperature of 4° C. and FIG. 6B shows pH at a storage temperature of 24° C.

DETAILED DESCRIPTION OF THE PREFERRED EMBODIMENTS

Figure 3:
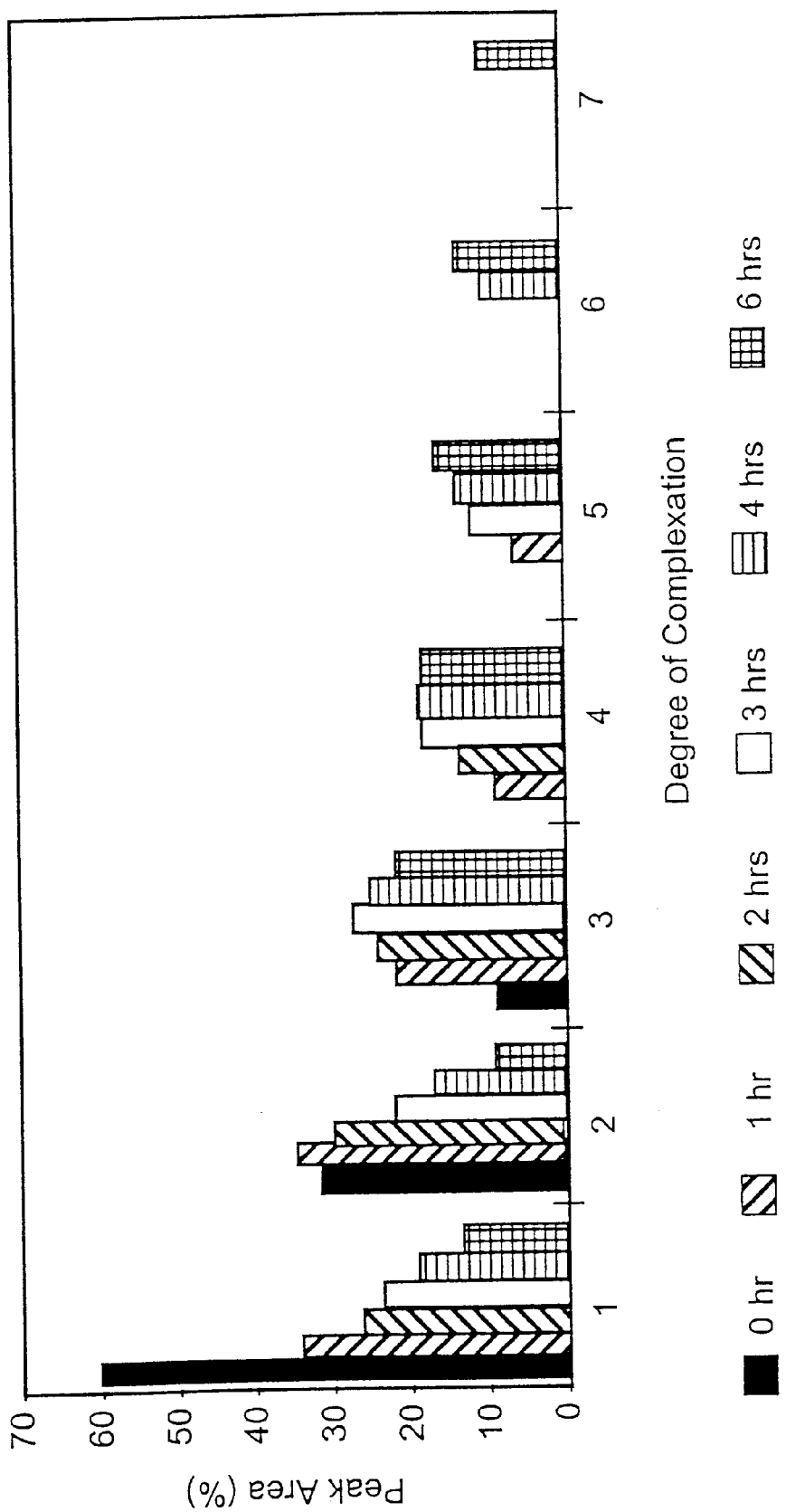
FIG. 3 is a graph showing the relationship of the degree of complexation to processing time at 4 mm Hg and 120° C., as measured by gel permeation chromatography (GPC).
Figure 4:
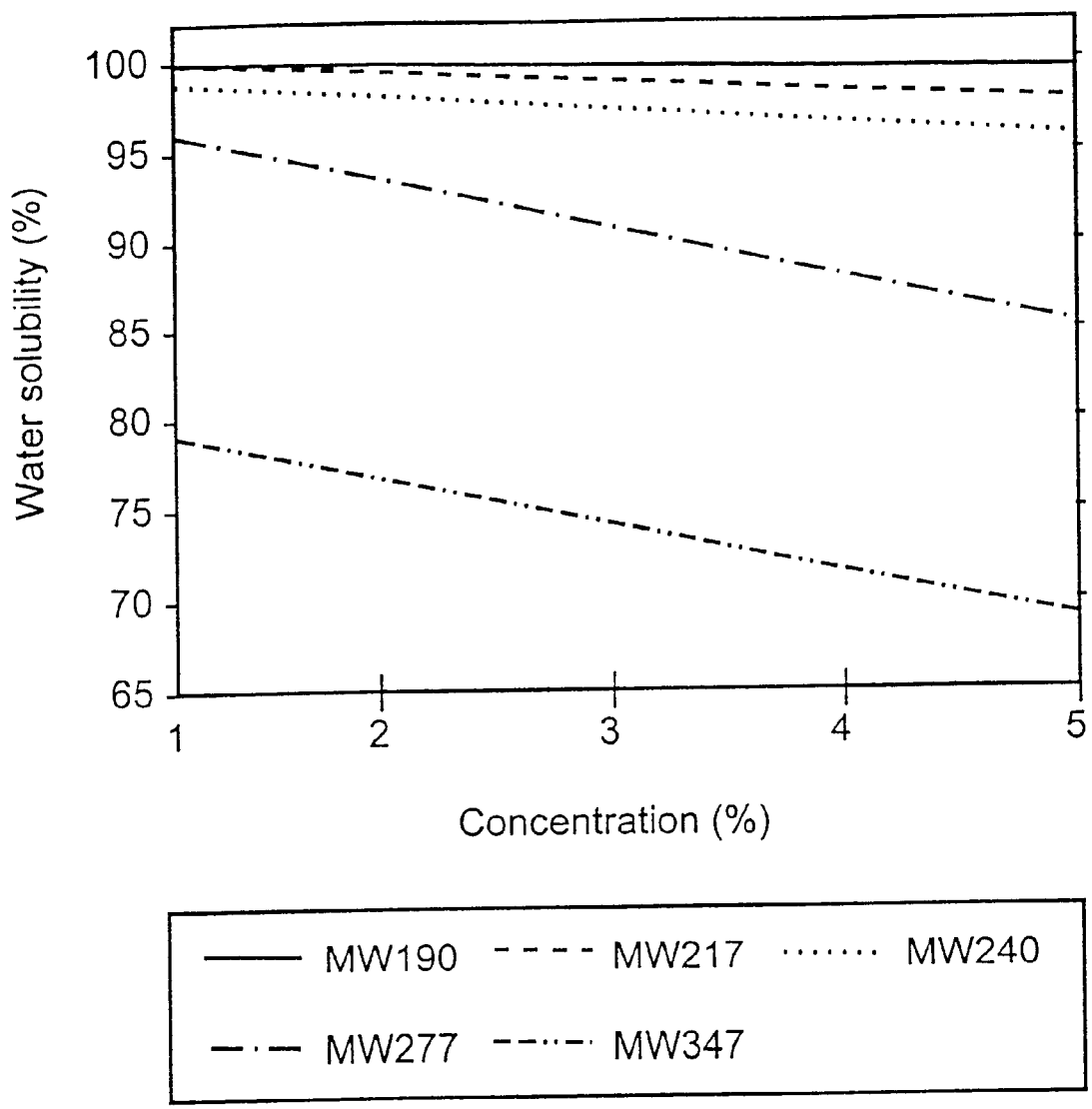
FIG. 4 is a graph showing regression lines of water-solubility of heat-treated lactic acid at 25° C. Regression coefficients: 0.97 (MW 190), 0.99 (MW 217), 0.92 (MW 240), 0.92 (MW 277), and 0.92 (MW 347).

The heat-treated lactic acid compositions of this invention comprise single lactic acid molecules (monomers) and more than about 50 weight percent, preferably more than about 75 weight percent, complexes of lactic acid monomers linked via ester linkages having from two to ten molecules per complex, and preferably from two to eight molecules to complex. They are water soluble and have a viscosity less than about 1.05 centistokes, preferably less than about 1.00 centistokes, in solutions having a concentration of about 2.5 weight percent.

The average molecular weight of these compositions is less than or equal to 700 D, and is preferably less than or equal to about 300 D, and most preferably is about 240 D, as determined by gel permeation chromatography (GPC). Heat-treated lactic acid having an average molecular weight of less than or equal to 700 D is water-soluble and analogous to carbohydrates having two to eight units. Relative solubility in water decreases with increasing molecular weight and concentration, while that in organic solvents increases.

The solutions increase in viscosity slightly with concentration but not molecular weight.

The isomers of lactic acid, i.e. L-lactic acid and D-lactic acid may be used for this process, as may optically neutral mixtures of these isomers.

The compositions produced by the heating process of this invention conducted at 4 mm Hg and 120° C. have the following components in the following preferred proportions:

monomeric lactic acid, about 20 to about 25% (peak area as measured by GPC);

dimeric lactic acid, about 18 to about 23% (peak area as measured by GPC);

trimeric lactic acid, about 25 to about 30% (peak area as measured by GPC);

tetrameric lactic acid, about 15 to about 20% (peak area as measured by GPC);

pentameric lactic acid, about 8 to about 13% (peak area as measured by GPC); and hexameric lactic acid, about 6 to about 11% (peak area as measured by GPC);

and also contain some complexes having seven to ten monomers.

Preferably, the trimeric component predominates in the composition, i.e. the most abundant component is trimeric lactic acid. In addition to the lactic acid complexes with ester linkages, some lactide (ring structures) molecules may also be present. It is preferred that lactides be kept to a minimum, e.g., less than about eight percent.

For use as disinfectants for reduction of microbial populations on surfaces, these compositions are preferably diluted to form aqueous solutions containing about 1 to about 10 weight percent of the lactic acid material, preferably less than about 5 weight percent, and more preferably, less than or equal to about 2.5 weight percent. Solutions containing between 0.5 to 1.0 or 2.0 weight percent lactic acid materials are especially useful in this invention.

Such aqueous solutions have a pH between about 2 and about 3, and maintain low pH for a longer period of time than lactic acid alone, retarding microbial growth for 24–48 hours, up to about 56 days. Surfaces treated with these solutions should be stored at normal refrigeration temperatures or below as increasing the storage temperature decreases the time during which lowered surface pH is maintained. The lactic acid complexes are stable at 25° C. for more than two days. After that, substantial hydrolysis may occur causing the lactic acid complexes to break down to form solutions having a higher percentage of monomers.

Allowing the surfaces to dry during storage helps prevent hydrolysis. In view of the stability of these solutions, they can be made up for use at the beginning of the work day and used without major changes.

The aqueous solutions of heat-treated lactic acid of this invention may be applied to the surface to be treated by any means known to the art including spraying, painting, and immersion of the surface into the solution.

In addition, the solutions may be added to particulate food materials such as chopped meat, ground meat, or sausage during normal processing.

The heat-treated lactic acid compositions of this invention may additionally be used in microencapsulated form using techniques and coatings known to the art, e.g.: gums such as gum arabic, agar, sodium alginate and carageen; carbohydrates such as starches, dextran, sucrose and corn syrup; celluloses such as carboxymethylcellulose; lipids including wax, paraffin, and stearic acid; inorganic materials such as calcium sulfate, silicate and clays; and proteins such as gluten, casein, gelatin and albumin. These materials can be used to coat surfaces on which reduction of microbial counts is desired to enhance the duration of pH reduction and anti-microbial activity.

In concentrated solutions of heat-treated lactic acid, e.g. above about 18 weight percent, autoesterification occurs. The percentage of complexes having larger numbers of molecules increases. During storage for nine months at 25° C., the molecular weight increases; however, the rate of change in molecular weight decreases with time. Thus concentrated solutions can be manufactured at another site, shipped and stored for reasonable lengths of time with only minimum change. Some hydrolysis of complexes containing multiple lactic acid monomers occurs when the concentrated solutions are diluted.

Lactic acid which has not been heat-treated, including commercially available solutions of lactic acid (having a concentration of approximately 88 weight percent), also undergo autoesterification. If pure lactic acid is stored as a syrup at room temperature, it will spontaneously commence intermolecular reactions with the formation of water and esters and, after a period of time, an equilibrium mixture containing about 6 weight percent water, 47 weight percent free lactic acid, and 47 weight percent lactic acid complexes with a mean number of lactic acid units per complex of 2.8 is obtained.

Reduction of microbial contamination on a surface is accomplished by treating a surface with an aqueous solution described above. The microbial population of the surface thereafter is less than that obtainable by applying the same concentration of commercial lactic acid in aqueous solution as a control solution, preferably by at least an order of magnitude. The microbial population of the treated surface may remain less than that of the control-treated solution for periods of 24 hours or more, up to about 56 days.

Aqueous solutions of about 0.5 to 2.5 weight percent of the heat-treated lactic acid compositions of this invention are preferably used to treat the surfaces of meat carcasses, such as beef, lamb, pork or poultry carcasses by spraying. The solution is preferably a 2.0 weight percent solution of heat-treated lactic acid having a molecular weight of about 240 D heated, preferably to a temperature of about 50° C., sprayed at a pressure of about 250 psi for about 10 seconds, preferably less than 20, seconds. A 5015 nozzle size was used in pilot scale testing to determine the foregoing optimum conditions. Temperatures of room temperature to about 80° C. are preferred. Oscillations of the nozzle of 70 cycles per minute were also found to be optimal.

The process for making the heated lactic acid compositions of this invention comprises subjecting a concentrated aqueous solution of lactic acid, above about 18 weight percent lactic acid and more preferably about 88–90 weight percent lactic acid or above, to conditions of temperature and/or vacuum pressure sufficient to drive water from said solution.

The formation of lactic acid complexes is accelerated by removal of water, including free and bound water released during esterification. This process is enhanced by starting with higher concentrated solutions of lactic acid, higher temperatures, reduced pressures (vacuum), and entraining agents such as nitrogen gas, or high-boiling, water-withdrawing agents such as xylene. Most of the water may be removed at temperatures ranging from 110–250° C. under vacuum (0–5 mm Hg). The limitation to water removal is the increasing viscosity in the reaction medium. The temperature should not be so high as to convert lactic acid or its complexes to the lactide.

Formation of lactic acid complexes can be conducted with or without catalysts such as toluenesulfonic or sulfuric acid or acid ion-exchange resin; however, catalysts known to promote lactide formation should be avoided. In the absence of an externally added strong acid, the lactic acid monomer acts as its own catalyst for the self-catalyzed complex formation. Preferably the process is conducted without added catalysts.

Preferred lactic acid starting materials for the process are lactic acids derived from starches such as cornstarch. These lactic compositions are typically available in concentrated aqueous solution containing about 88–90 weight percent lactic acid. Typical lactic acid preparations including commercially available lactic acid preparations are not in pure monomeric form, but due to the equilibrium reactions described above, typically contain some ester complexes. Commercially available food grade lactic acid may contain up to 47 weight percent complexed lactic acid formed due to heating during processing, but without the heat treatment as described herein will not contain greater than 50 weight percent complexed lactic acid.

The properties of heat-treated lactic acid with a molecular weight of 240 are greatly affected by its molecular weight and concentration. The molecular weight of heat-treated lactic acid is linearly related to polymerization time, and the final molecular weight is repeatable when the temperature, time, vacuum, and initial concentration of lactic acid are controlled.

Without wishing to be bound by any particular theory, applicants believe the compositions of this invention work to provide improved reduction of microbial contamination by providing an acidic environment over a longer period of time than uncomplexed lactic acid, as the complexes hydrolyze and break down to form lactic acid monomers. Further, the compositions of this invention are more hydrophobic than previously-used lactic acid solutions, and thus may more easily penetrate cell membranes to reduce microbes within the cells of food surfaces being treated. An increase of molecular weight of polylactic acid increases hydrophobicity of the molecule. Like a fatty acid, heat-treated lactic acid containing ester complexes more easily attaches to the bacterial cells than lactic acid, associates with the membrane and disrupts its functions. Hydrophobicity also facilitates penetration of the heat-treated lactic acid into the cell where subsequent hydrolysis results in acidification of the cytoplasm. Low molecular weight oligomers contain one free carboxylic acid group on the terminal lactic acid molecule. In an aqueous environment this group undergoes hydrolysis of ester linkages, releasing additional acidity and functions as a latent acidulant or slow release acidulant. Hydrolysis of heat-treated lactic acid has been found to be significantly affected by temperature and concentration. Raising the temperature or using a lower concentration resulted in increased rates of depolymerization. The solubility of heat-treated lactic acid in water is reduced at about MW 600 and with increasing concentration range from 1–5%.

EXAMPLES

Experimental work showed that the average molecular weight of heat-treated lactic acid was linearly related to polymerization time at 120° C. and 4 mm Hg. The properties of this material were affected by its molecular weight and concentration. Solubility in water decreased with increasing molecular weight and concentration. Viscosity of solutions of this material increased when the concentration increased.

The pH of such solutions decreased as the concentration increased; the differences were less when molecular weight increased. Both total lactic acid and normality were related to the concentration of the solution. At the same concentration of heat-treated lactic acid or lactic acid the solution with higher molecular weight had higher total lactic acid and the lower normality.

Hydrolysis of heat-treated lactic acid was significantly affected by temperature and concentration. Raising the temperature or diluting to a lower concentration resulted in increased rates of depolymerization. The rate of release of monomeric lactic acid was higher initially, then decreased after the first 24 hours. The average molecular weight increased slightly when a concentrated solution was stored for nine months at room temperature. Some commercial lactic acid samples have a relatively high concentration of esterified lactic acid complexes because of autoesterification.

Heat-treated lactic acid having a molecular weight of 240 is more effective in maintaining a low pH on the surface of beef meat plate and in ground meat than other molecular weights of heat-treated lactic acid or lactic acid per se.

The pH of the meat surface was affected by molecular weight and concentration of heat-treated lactic acid, dipping frequency and time, storage temperature and encapsulation in starch. Higher concentrations resulted in lower pH on the surface of plate meat.

Normality was a better indicator of initial pH while concentration (weight percentage) expressed more precisely the total acid released. Diffusion of acid into the meat was indicated by decreasing pH at 5 and 10 mm below the surface while pH at the surface increased. Increasing the dipping time only slightly improved the maintenance of a low pH. Double dipping resulted in a lower overall pH than a single dip. Dipping first with lactic acid then heat-treated lactic acid had the same impact on pH as using a higher concentration of heat-treated lactic acid. Increasing storage temperature shortened the cycle time, apparently by promoting hydrolysis of complexes, diffusion of free lactic acid, buffering by basic materials in the meat, and growth of microorganisms. Encapsulation of heat-treated lactic acid in starch lengthened the time pH remained low in ground beef.

The storage time rather than concentration (up to 6%) was the major factor in changing the color of the meat surface.

Heat-treated lactic acid was more effective than lactic acid in inhibiting *E. coli* and *E. coli* O157:H7 both in broth culture and on the meat surface. A higher reduction of bacteria was seen on beef plate meat when a 1% solution of heat-treated lactic acid was used compared to lactic acid. The heat-treated lactic acid treatment caused a maximum reduction of ca. 2 logs in 48 hours. The pH values maintained a reduction for 72 hours at 4° C. At 72 hours, a 0.70 reduction of pH occurred. Heat-treated lactic acid is more effective than lactic acid in reducing the numbers of *E. coli* on the surface of meat stored at 4° C. for 24 hours. In ground beef, 2% solutions of lactic acid and heat-treated lactic acid maintained a low pH for up to ten days, and subsequent days revealed pH values of samples with heat-treated lactic acid increased but still lower than the lactic acid treatments. The use of heat-treated lactic acid is useful as a meat decontaminant during processing operations. Due to its physical properties, heat-treated lactic acid is an effective antimicrobial treatment for meat.

Heat-Treatment of Lactic Acid

Commercial grade lactic acid in aqueous solution comprising 88–90 weight percent lactic acid was heated to form esterified complex mixtures of this invention.

Figure 9:
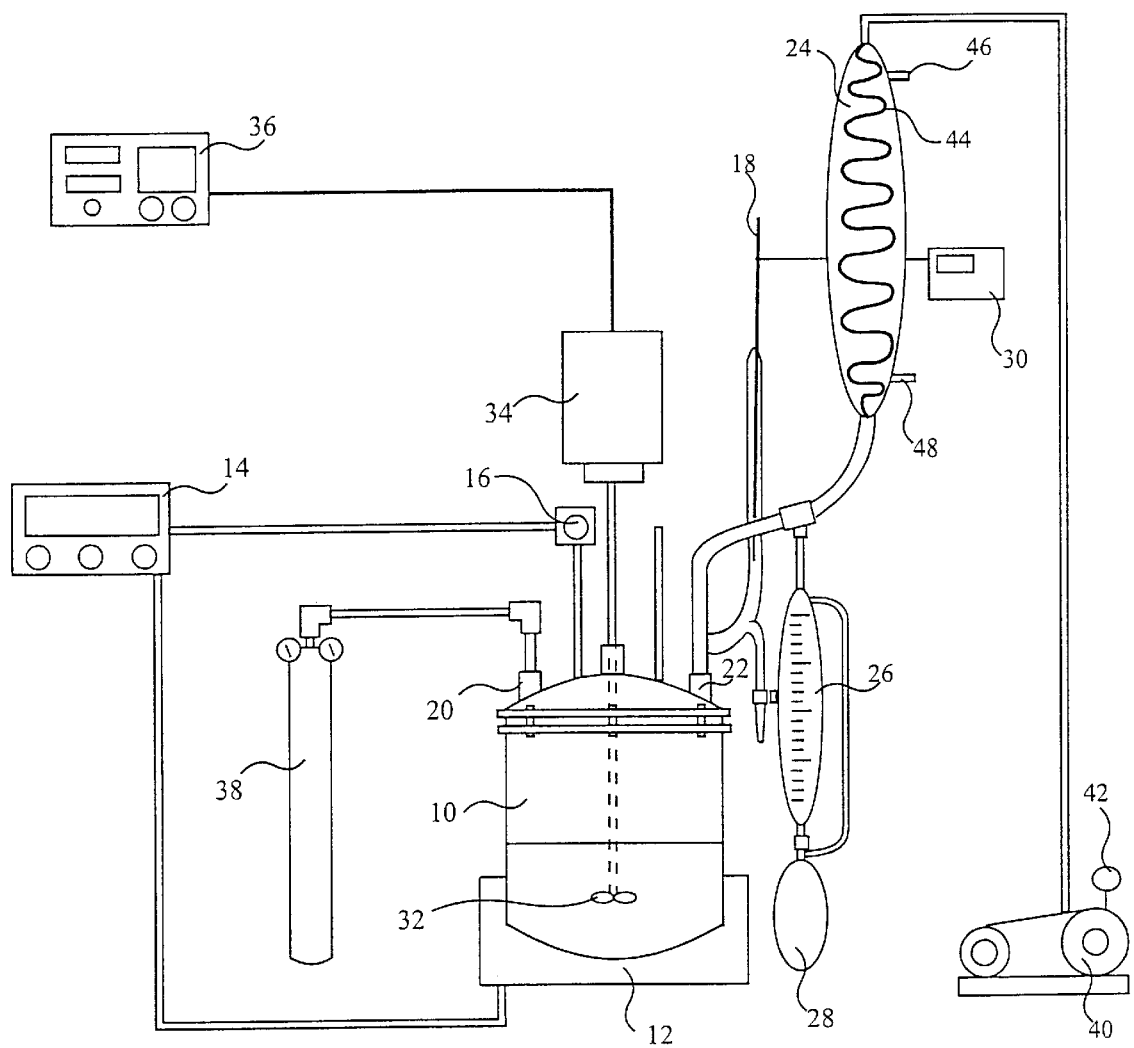
FIG. 9 is an apparatus used for the production of heat-treated lactic acid.

Heat-treated lactic acid was synthesized by direct polycondensation of this lactic acid without catalyst using a modification of the method described by Sorenson and Campbell (Sorenson, W. R. and Campbell, T. W. [1968], "Step polymerization" In: *Preparative Methods of Polymer Chemistry*, $2^{nd}$ ed. John Wiley & Sons, New York, N.Y., pp. 134–136). A 500 mL reaction vessel 10, shown in FIG. 9, was heated by a jacketed mantel 12. The temperature was controlled by a temperature control unit 14 that consists of a transformer temperature controller (Model CN 9121, Omega Engineering, Inc., Stamford, Conn.) and thermocouple 16 (Type J, Omega Engineering, Inc.). The reaction vessel was equipped with a gas inlet 20 connected to nitrogen source 38, an outlet 22, a thermometer 18 connected to outlet 22 and to temperature readout 30, a cooling water condenser 24 with graduated funnel 26 and flask 28 for collection of condensate, and a stirrer 32 (Servodyne Model L-50000–20) controlled by a motor 34 connected to a stirrer controller 36. The condenser 24 is equipped with cold water coil 44 and water inlet 46 and water outlet 48. A vacuum pump 40, a PS Model 25 pump (Precision Scientific Co., Chicago, Ill.) with a vacuum gauge 42 (0–760 mm Hg) (Fischer Scientific Co., Pittsburgh, Pa.) was connected to reactor outlet 22.

The reaction vessel 10 filled with 88% L(+) lactic acid (ADM, Decatur, Ill.) was flushed with prepurified nitrogen gas from nitrogen source 38 through gas inlet 20 for 15 minutes prior to each polymerization reaction. The polymerization was carried out in vacuum produced by activating vacuum pump 40 (ca. 4 mm Hg) while stirring at 70 rpm with stirrer 32 at 120° C., achieved by adjusting the temperature of activated mantel 12 with temperature control unit 14. Heat-treated lactic acid of the desired molecular weight was obtained by varying polymerization time. To determine the effect of reaction time, polycondensation was carried out in separate runs for 15 minutes, 30 minutes, and 1, 2, 3, 4, 6 and 8 hours.

Gel permeation chromatography (GPC), also called gel filtration chromatography, is liquid-solid elution chromatography that separates polymers into fractions by means of the sieving action of a cross-linked polystyrene gel or other sieve-like packing. The polystyrene gel, which serves as the stationary phase, is commercially available with a wide distribution of pore sizes (1 to $10^6$ nm). Since the smaller molecules permeate the gel particles preferentially, the highest molecular weight fractions are eluted first. Thus, the fractions are separated on the basis of size by GPC.

A solution with a solvent such as tetrahydrofuran (THF) and the solvent (THF) are pumped through separate columns at a rate of about 1 ml/min. The differences in refractive index between the solvent and solution are determined by a differential refractometer and recorded automatically. Each column unit must be calibrated using polymers of known molecular weights (standards).

A Waters Model 150-C ALC/GPC was used in this experiment. The column temperature was 35° C. and the flow rate was one ml/min. The columns were 500 A, 1000 A Waters ultrastyragel and two 100 A Phenomenex ultrastyragel columns in series. The mobile phase was tetrahydrofuran (THF) (HPLC grade, Fisher Scientific Co.). The standard was poly(ethylene glycol) (106, 200, 500 1000,1500, 5000 MW) (Polysciences, Inc.). Data were analyzed using a Spectra Physics Model SP4270 integrator equipped with a GPC module.

The molecular weight of the heat-treated lactic acid increased with increasing process time at 120° C. and 2 mm Hg ($r^2$=0.99) (FIG. 2). Since complex formation is accomplished by removing the water, the final molecular weight or degree of complexation is dependent on temperature, time, vacuum, and initial concentration of lactic acid. Nevertheless, synthesis of known low molecular weight heat-treated lactic acid is predictable and repeatable.

An equilibrium is obtained by heating at 100° C. for about ten hours. This time is sufficient for the formation of the required number of ester bonds, forming lactic acid, lactoyllactic acid (the dimer, lactoyllactoyllactic acid (the trimer) and lactoyllactoyllactoyllactic acid (the tetramer).

At short process times, a product with a lower degree of complexation (DC) dominated (FIG. 3). With increasing process times, the percentage of low DC decreased and that of higher DC increased. This implies that lactic acid, lactoyllactic acid, higher chain lactic acid complexes, and water were all in a dynamic equilibrium at each process time. Since the heat-treated lactic acid is not a single chain of complexed lactic acid, the molecular weights measured by GPC in FIG. 2 are not values exactly equivalent to DP1, DP2, DP3, etc.

The product was a water-soluble mixture of monomeric lactic acid and complexes of lactic acid in ester linkage comprising from 1 to 8 molecules per complex. These complexes contain one free carboxylic acid group on the terminal lactic acid molecule with the other acid groups bound in ester linkage.

Hydrolysis of Lactic Acid

Concentrated (90%) commercial L-lactic acid was diluted to 0.5% and heated at 95° C. up to 32 hours. The free monomeric lactic acid in the solution increased from 84% to 100% while complexes decreased from 16% to 0%. If concentration was increased, the time needed for complete hydrolysis also increased. At the 10% level after 44 hours there still existed two GPC peaks even though much longer time was used than at the 1% level.

Measurement of Viscosity and Water-Solubility

Solutions with different concentrations of the heat-treated lactic acid product of this invention (w/w) were made and vacuum-filtered. The filter paper was dried at 120° C. for 24 hours, then put in desiccator for four hours before weighing. The weight of filter-paper before filtering and after drying was recorded. The water-solubility was calculated by the following equations. The results are the average from equation (1) and equation (2) with two measurements of each method:

$$\text{Solubility} = \frac{W_t(1) - (W_t(2) - W_t(3))}{W_t(1)} \times 100\% \quad \text{Equ. (1)}$$

$$\text{Solubility} = \frac{W_t(4) - W_t(5)}{W_t(4)} \times 100\% \quad \text{Equ. (2)}$$

where $W_t(1)$ is the weight of acid added to the solution, $W_t(2)$ is the weight of filter paper after drying, $W_t(3)$ is the weight of filter paper before filtering; $W_t(4)$ and $W_t(5)$ are the solutions before and after filtering, respectively. After filtering, the solutions were used to measure viscosity.

An Ubbelohde Viscometer (Industrial Research Glassware Ltd., USA) was employed to measure the viscosity of the acid solution at 25° C. The afflux time was recorded and the viscosity of the samples was calculated by multiplying the afflux time by the viscometer constant.

Lactic acid is completely miscible with a great number of solvents, including water, ethanol and ethyl ether, and esterified lactic acid complexes and polylactides of intermediate to large chain length are soluble in all common solvents except petroleum and water. Unfortunately very little information is available about solubility of very low molecular weight esterified polylactic acid complexes in water. The water-solubility and viscosity of this material is needed in order to calculate the appropriate spraying pressure, nozzle size, etc.

The water-solubility (%) of the heat-treated lactic acid product is dependent on concentration ($p<0.01$) and molecular weight (p<0.00 1) in the range expected to be used in industry (1%–5%, w/w) (FIG. 4). Increasing concentrations at the same molecular weight or increasing molecular size at the same concentration level reduced the water-solubility. Thus, the highest concentration (5%) with highest molecular weight tested (MW 347) had the lowest relative water solubility. Probably this is because the complexed material with higher molecular size is more hydrophobic, and the solution with higher concentration had higher percentage of complexes with higher molecular weight.

As is found with many substances, the viscosity of heat-treated lactic acid solutions is proportional to the concentration ($p<0.001$).

The data on viscosity were not affected by molecular weights ($p>0.6$); however, the data were confounded by the higher molecular weight materials being less soluble. There would be less complexed lactic acid in the solution after filtering.

Measurement of pH of Meat Surfaces

The pH value is an important characteristic of sanitizers. Higher concentrations of heat-treated lactic acid have lower pH values than lower concentrations.

Solutions of acids (lactic acid and heat-treated lactic acid of this invention) were prepared in distilled water. All solutions were freshly made.

One piece of meat was hooked with a fish-hook and dipped in 200 ml of acid solution for 15 or 30 seconds, then hung in a stainless steel basket which was wrapped with aluminum film. The storage temperature was controlled at 4, 10, 18 or 25° C.

The pH of the meat surface was measured at initial (just before dipping, 0 time), immediately after dipping, four hours, 24 hours, etc. Each treatment consisted of five samples randomly selected with two pH readings per sample.

The pH of meat surfaces was determined with a pH meter (Beckman Instrument Inc., Calif.) and a surface combined pH electrode (Fisher Scientific, Inc., N.Y.). A drop of deionized water was placed on the meat and a surface pH probe was pressed to the wetted surface until a stable reading was obtained. There was no statistical difference between the pH with and without one drop of water on the meat surface (p>0.899) if the surface of the meat was not dry.

When meat was dipped in a 0.5% heat-treated lactic solution of this invention and stored at 4° C., the acid lowered the pH of the meat surface to 5.15, then the pH rose to around 5.7 after 24 hours. After that, the change in pH was dependent on the treatment. The pH of the controls rose faster than all other treatments. Heat-treated lactic acid (MW 240) maintained a low pH for the longest period of time (up to 100 hours), which was statistically different from the controls. Heat-treated lactic acid (MW 217 and MW 277) had higher pH values than MW 240 but were also significantly different from the control for most of the periods. The treatment with lactic acid also maintained a lower pH than the control although it was higher than MW 240 and MW 217. Progressively higher molecular weight heat-treated lactic acid was not more efficient in keeping a lower pH for a longer time.

Figure 5:
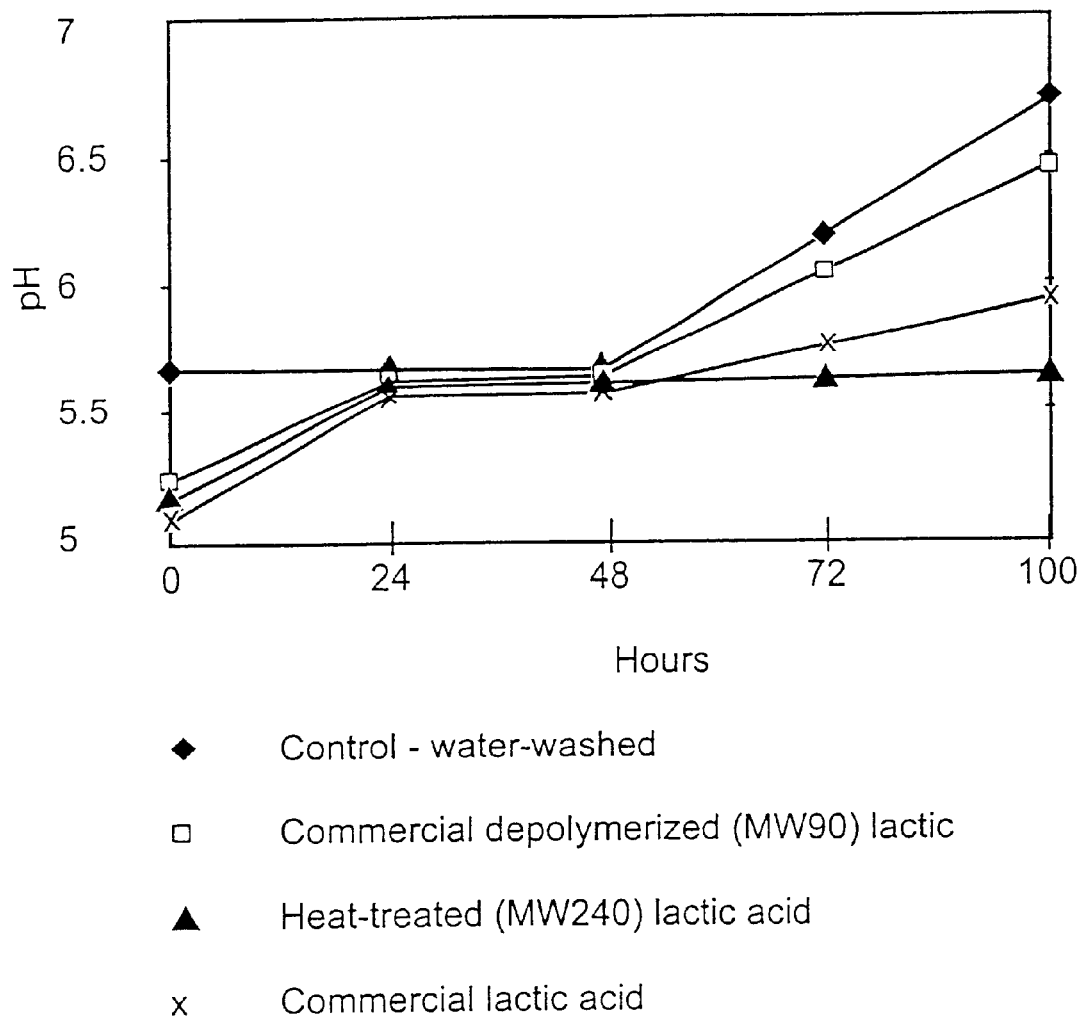
FIG. 5 is a graph comparing the effects of lactic acid, plain water control and heated lactic acid on pH on a carcass surface.

FIG. 5 compares the pH on beef surface obtained using a wash of de-ionized water (control), and 1% solutions of commercial lactic acid of MW 90 pretreated to depolymerize any ester complexes present, heat-treated lactic acid of this invention (MW (0 240) and commercial lactic acid containing some complexation but less than about 47% due to heating during processing. pH values below about 4.5 are best for sanitation.

Measurement of pH Profile within Meat

Polylactic acid (PLA) (MW 3500) was used to see if PLA at this molecular weight would be more or less effective in lowering the pH of ground beef than heat-treated lactic acid of this invention. PLA (MW 3500), heat-treated lactic acid (MW 240) and lactic acid was mixed with ground beef at 2% (w/w) level and the mixture stored at 4° C. Both heat-treated lactic acid (MW 240) and lactic acid maintained a low pH (less than 4) for up to ten days; after that, heat-treated lactic acid (MW 240) had a lower pH than lactic acid.

There was no difference in the meat pH between the control (without acid added) and with addition of PLA (MW 3500) during the storage time. This is due to the poor water solubility of PLA, i.e., the PLA Could not be hydrolyzed into free lactic acid; consequently, it could not reduce the pH of the meat.

Figure 6A:
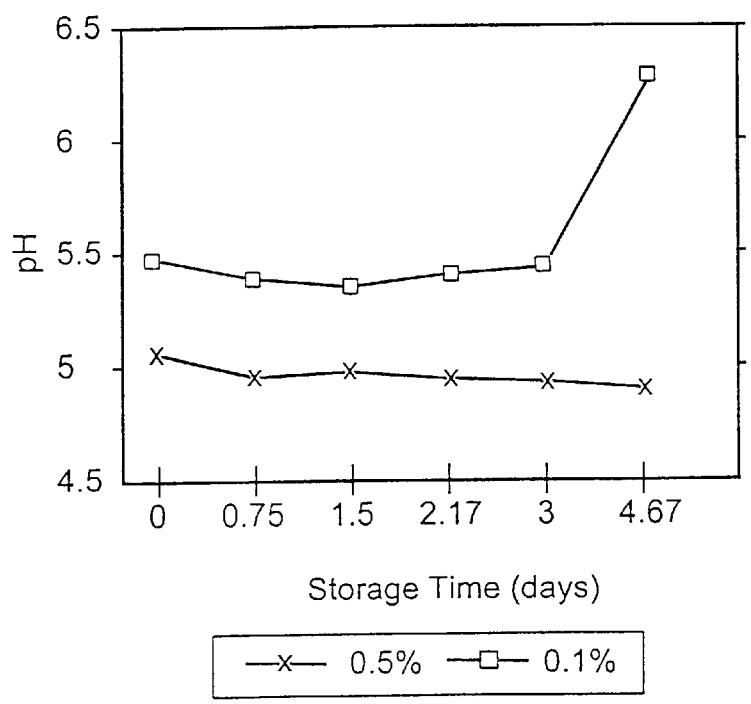
FIGS. 6A–B are graphs showing the effects of concentration of heat-treated lactic acid (MW 240), temperature and time on the pH of ground beef.
Figure 6B:
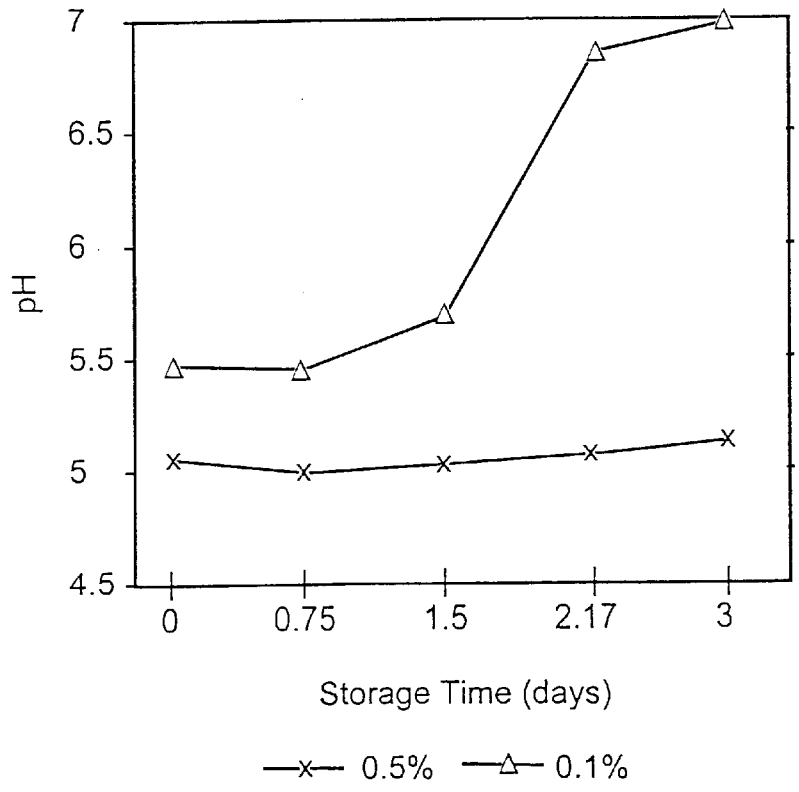

Heat-treated lactic acid (MW 240) is better than lactic acid in controlling pH in ground beef but the effects are temperature-dependent. At 4° C., heat-treated lactic acid (0.5 and 0.1%) and lactic acid maintain pH at a low level for over 5.5 days. At room temperature (24° C.) and 0.5%, heat-treated lactic acid is better than lactic acid after three days. With 0.1% acid, differences are seen after three days at 4° C., but only 1.5 days at room temperature. These results suggest that there is an interaction between concentration of acid and storage temperature in controlling the meat pH. Increasing concentrations of heat-treated lactic acid are more effective in controlling the pH of meat (See FIG. 6).

Meat Contamination and Decontamination

Core samples of beef plate meat, attached individually to wire hooks, were dipped for 15 seconds into inocula of manure, *E. coli* C5 or *E. coli* O157:H7. The dipped meat was allowed to air dry for 15 minutes, after which it was submitted to decontamination treatments. Samples with no further treatment and samples dipped in water were negative and positive controls. The dipping time for each treatment was 30 seconds. After treatments, meat pieces were hung in a stainless steel basket, wrapped with aluminum foil and stored at 4° C. for 24 hours.

Each sample was placed in a Stomacher bag with 99 mL 0.1% peptone water and homogenized for two minutes before plating. Dilutions were made and 0.1 mL of appropriate dilution was plated onto three plates for each medium: standard methods plate count agar (SPCA), tryptic soy agar (TSA) and violet red bile agar (VRBA). After plating and 15 minutes for recovery, the TSA and VRBA plates were overlaid with 12 mL of VRB agar. The plates were incubated at 37° C. for 20 hours. The colonies were counted using a Quebec Colony Counter (American Optical). The number of stressed organisms was determined by subtracting the count on VRBA overlaid with VRBA from the count on TSA overlaid with VRBA.

Inhibition of *E. coli* O157:H7 on Meat Surface

Heat-treated lactic acid is more effective than lactic acid or water in reducing the numbers of *E. coli* and spoilage organisms on the surface of artificially-contaminated meat stored at 4° C. for 24 hours (Table 1). Differences among the negative control (without dipping), positive control (dipping with water), and treatments with lactic acid or heat-treated lactic acid were all significant. Plate count agar (SPC) enumerates both *E. coli* and spoilage organisms. Growth on tryptic soy agar followed by an overlay of violet red bile (TSA/VRBA) allows stressed organisms to recover but still selects for *E. coli*. The number of organisms found on violet red bile agar (VRBA) was less than TSA/VRBA because of the failure of more stressed organisms to grow.

Heat-treated lactic acid reduced the numbers of organisms more than the other treatments. Water washing (dipping) reduced counts of spoilage organisms and stressed *E. coli* over 50%. Differences were greater (60%) when organisms were not permitted to overcome stress.

The correlation coefficients between microbial count and pH value are 0.69, 0.79 and 0.71 for SPCA, TSA and VRBA, respectively. These results imply again that there may be other factors besides pH, probably hydrophobicity, affecting the microbial growth on the meat surface just as in the pure cultures.

TABLE 1

Population of E. coli 0157:H7 and pH value on meat surface affected by treatments[1,2,3]

| Treatment | SPC[4] | | TSA[4]/VRBA | | VRBA[4] | | Injured cells[4] |
|---|---|---|---|---|---|---|---|
| | Count | pH | Count | pH | Count | pH | |
| Control[5] | 20.4 | 5.71 | 18.3 | 5.92 | 14.6 | 5.99 | 3.6 |
| Water[6] | 11.2 | 5.89 | 9.6 | 5.96 | 6.1 | 6.0 | 3.5 |
| 1% LA[7] | 7.0 | 5.22 | 6.0 | 5.40 | 3.7 | 5.08 | 2.3 |
| 1% heat-treated LA[8] | 4.7 | 5.24 | 4.3 | 5.19 | 2.8 | 5.17 | 1.5 |

[1]Contamination 15 sec; decontamination 30 sec; stored at 4° C. for 24 hours; incubation 20 hours at 37° C.
[2]Population unit: CFU/cm$^2$ × 10$^6$.
[3]Means in the same column with different superscripts are significantly different as p <0.01.
[4]Means of 45 determinations: 5 pieces of meat/treatment, 3 plates/meat, 5 repeatments.
[5]Without dipping.
[6]Dipping with water.
[7]Normal lactic acid.
[8]Average Molecular Weight: 240

Both the molecular weight and the concentration of heat-treated lactic acid affected the growth of a nonpathogenic strain of *E. coli* (C5). Increasing the concentrations of lactic acid or heat-treated lactic acid increased the lag phase and decreased the growth rate. Heat-treated lactic acid is more effective in inhibiting *E. coli* than lactic acid at the 1% level. At lower (0.45%) or higher (1.8%) concentrations, the growth of E. coli with heat-treated lactic acid was less than that with lactic acid, but the difference was not significant. The control was always significantly different in pH from other treatments.

Figure 7:
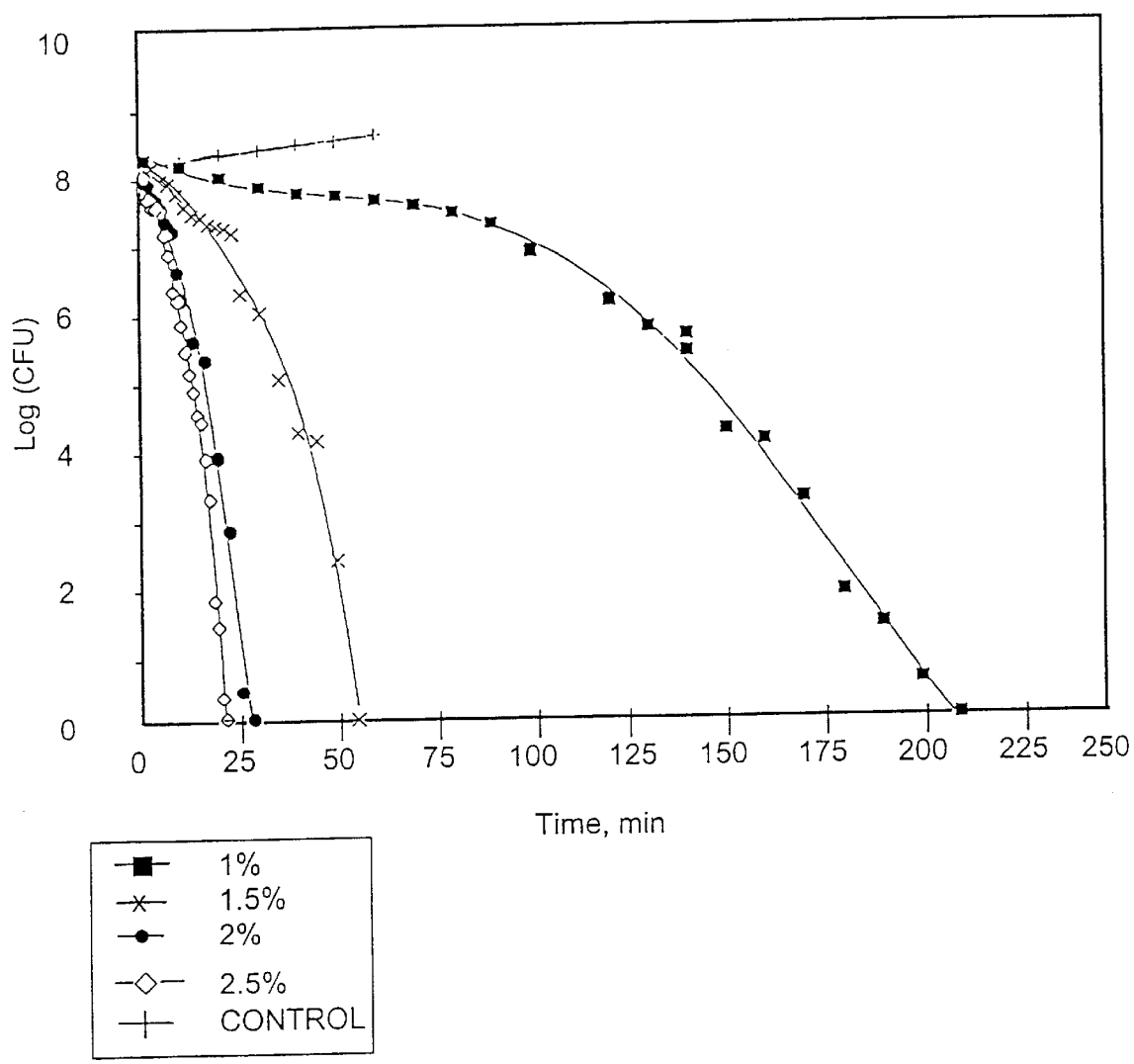
FIG. 7 is a graph showing variation of $E.$ $coli$ O157:H7 population with concentration of heat-treated lactic acid in broth culture.
Figure 8:
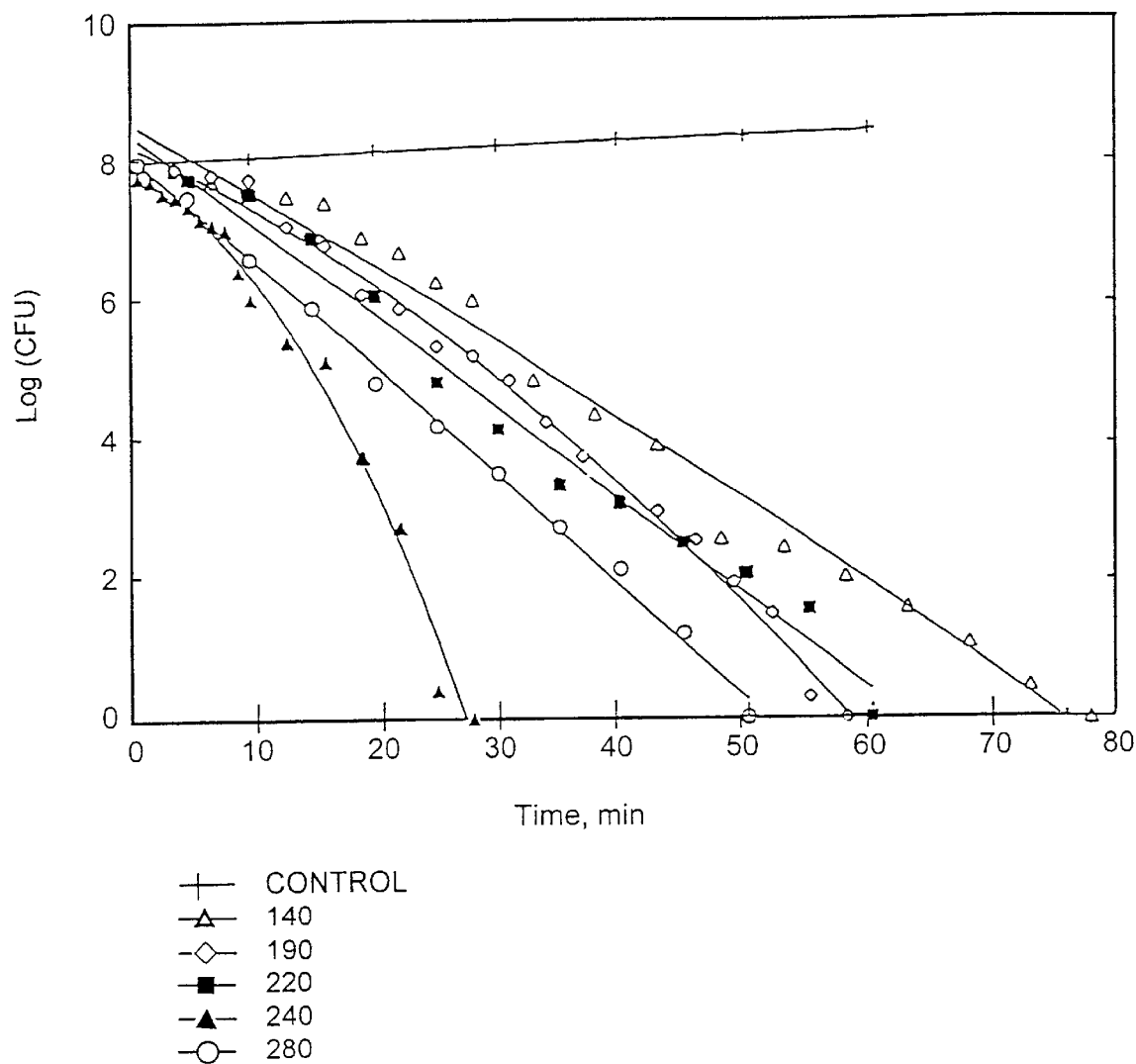
FIG. 8 is a graph showing variation of $E.$ $coli$ O157:H7population with molecular weight of heat-treated lactic acid at 2 weight percent concentration in broth culture.

Heat-treated lactic acid was more effective than lactic acid in inhibiting E. coli O157:H7 as with strain C5 except a higher amount of acid is required. E. coli O157:H7 is comparatively resistant to effects of temperature and concentration of lactic acid. If a sanitizing procedure is capable of causing decrease in the E. coli population, then it should reduce numbers of other bacteria by an equal or larger amount. FIGS. 7 and 8 show effects of concentration and molecular weight on number of E. coli O157:H7.

High Pressure Liquid Chromatography showed that heat-treated lactic acid disappeared on the surface of meat within four days. Experiments also showed that microbial reduction is greater on fat tissue than on lean tissue and is correlated with pH on both fat and lean surfaces and that beef plate meat treated with 2.0% heat-treated lactic acid displays temporary discoloration.

Pilot Test of Carcasses

Heat-treated lactic acid having a molecular weight less than or equal to 700 of this invention was tested in a pilot scale carcass washing system (CAPER—Carcass Acquired Pathogen Elimination Removal) for removal of bacterial contamination. Beef plate meat was contaminated with dilute cattle manure and treated by spraying with water, lactic acid or the heat-treated lactic acid solutions of this invention. The effect of process parameters, such as spray pressure, nozzle size, nozzle oscillation, on bacterial removal were evaluated. Optimized parameters are shown in Table 2.

These tests showed that using optimized sprayer parameter settings and a 2 weight percent solution of heat-treated lactic acid having an average molecular weight of 240, a maximum five log reduction in bacterial count was achieved twenty-four hours after treatment on beef plate meat purposely contaminated with diluted cattle manure. Typical reductions reported in the literature for lactic solutions are in the range of one to two logs. Conditions of temperature, spray pressure, concentration, nozzle size and molecular weight significantly impacted reduction of bacterial counts while spray time and oscillation speed did not appear important in the ranges tested.

Corrosion

Corrosion of nylon, brass, tin, copper, aluminum, rubber, PVC, stainless steel, zinc, and painted hardware was evaluated after exposure to water, acetic acid, lactic acid and the heat-treated lactic acid of this invention having an average molecular weight 700 D or less by exposure in air, single dipping or immersion. The heat-treated lactic acid showed less corrosive effects than the other substances.

The results show that the heat-treated lactic acid of this invention is more compatible with equipment and facilities than acetic acid or lactic acid.

TABLE 2

| Optimized Parameters (Pilot-Scale Sprayer) | |
| --- | --- |
| Temperature (° C.) | 50 |
| Concentration (%) | 2 |
| Pressure (psi) | 250 |
| Nozzle Size | 5015 |
| Spray Time(s) | 10 |

TABLE 2-continued

| Optimized Parameters (Pilot-Scale Sprayer) | |
| --- | --- |
| MW | 240 |
| Oscillation (cycle/min) | 70 |

Analysis of Toxicity of Heat-treated Lactic Acid on Escherichia Coli O157:H7 in Ground Meat.

Inoculum Preparation

The cultures of Escherichia coil O157:H7 were acquired from the Centers for Disease Control and Prevention (CDC, Atlanta, Ga.). A five-strain mixture was used for all inoculation studies (Table 3). Cultures were preserved in freeze dried medium. Cells were resuscitated in tryptic soy broth (TSB: Difco Laboratories, Detroit, Mich.) at 37° C. and transferred again at 24 hours in tryptic soy broth to achieve the stationary growth phase.

The states of growth of E. coli O157:H7 were determined by removing 1.0 mL samples at one hour intervals for the first eight hours of growth, every two hours for the next eight hours, then every three hours over a 24 hour incubation period at 37° C. Serial dilutions (1:10) in sterile 0.1% peptone water (Bactopeptone, Difco Laboratories) were prepared, and appropriate dilutions (0.1 mL) were surface-spread in duplicate on MacConkey Sorbitol Agar (MSA; Difco Laboratories). Colonies were counted after 24 hours of incubation at 37° C. Absorbency and transmittance was read on a Spectrometer (Spectronic 20, Bausch & Lomb, Rochester, N.Y.) at 600 nm at each sample period.

TABLE 3

Escherichia coli strains donated to the University of Missouri-Columbia by the Centers for Disease Control and Prevention

| Strain # | Serotype | State, food | Shiga Toxin(s) | Diagnosis |
| --- | --- | --- | --- | --- |
| 3055-93 | O157:H7 | LA | II | hemolytic uremic syndrome |
| 3178-95 | O157:H7 | FL | II | hemorrhagic colitis |
| H2439 | O157:H7 | OR, Odwalla apple juice | I, II | N/A |
| C7927 | O157:H7 | MA, apple cider, human | I, II | bloody diarrhea outbreak |
| G5310 | O157:H7 | WA, Jack-in-the-Box meat isolate | I, II | outbreak |

Determination of Microbial Growth in Meat

Meat Contamination and Decontamination

Ground beef and ground pork was obtained from the University of Missouri-Columbia Food Science and Human Nutrition Department. Fresh pork sausage (Jimmy Dean Regular Pork Sausage, Cordova, Tenn.; Ingredients: fresh pork, ham, pork loin, water, salt, spices, sugar, monosodium glutamate) was purchased from a local grocery store. The fat content for ground beef, ground pork and breakfast sausage was determined by the modified Babcock method (Pearson, A. M. and Tauber, F. W. [ 1984] "Analytical methods," Ch. 16, In: Processed Meats, $2^{nd}$ ed., The AVI Publishing Company, Inc., Westport, Conn., pp. 375–376) with duplicate samples within three replications and was 25, 25 and 37% respectively. The meats were stored at −60° C. in 254 g chubs and thawed at 4° C. for 48 hours before use.

Heat-treated lactic acid solutions with a molecular weight of 240 were prepared at 1% and 2% concentrations (w/w). The cultures were activated by two successive transfers (24 hours each) into tryptic soy broth (TSB) and incubated at 37° C. One mL from each culture was transferred to a centrifuge tube to obtain a five-strain mixture and centrifuged for ten minutes at 10,000 rpm at 4° C. The supernatant was removed and the pellet was suspended in 30 ml of 0.1% peptone water. The mixture (2.5 mL) was added to 420 grams of ground beef, ground pork, and breakfast sausage, and each was mixed by gloved hands in a folding motion for two minutes. Each meat was then divided into 140 g portions for treatments. The control portion was mixed with 4 mL double distilled water. The 1% heat-treated lactic acid portion was mixed with 4 mL of the 1% heat-treated lactic acid solution. The 2% heat-treated lactic acid portion was mixed with 4 mL of the 2% heat-treated lactic acid solution. Each portion was mixed again by gloved hands in a folding motion for two minutes. The meat was then divided into sub-samples by meat type, treated, and placed in sterile plastic bags (Whirl-Pak Bags, Nasco, Fort Atkinson, Wis.).

Samples were stored at 4° C. Sampling was done after 1, 24, 72 and 168 hours (days 0, 1, 3, and 7).

Incubation and Counting

Meat samples (2 g) were homogenized with 20 mL 0.1% peptone water for one minute. Serial dilutions were made in 0.1% peptone water and appropriate dilutions were plated in MSA. Plates were incubated at 37° C. for 24 hours. Colonies were counted using a Model 900A Colony Counter (Banter, Burlington, Calif.) according to procedures recommended by Swanson et al. (Swanson, K. M. J. et al. [ 1992], "Colony count methods" In: *Compendium for the Microbiological Examination of Foods*, 3rd ed., American Public Health Association, Washington, D.C., pp. 75–94). Randomly selected isolates were serologically confirmed as *E. coli* O157:H7 using Bacto *E. coli* O antiserum O157, and Bacto *E. coli* H antiserum H7 (Difco).

Measurement of pH of Meat Slurries

Sample pH was determined according to the procedures of Koniecko (Koniecko, E. S. [1979] *Handbook for Meat Chemists*, $1^{st}$ ed., Avery Publishing Group Inc., Wayne, N.J.). Ten grams of meat sample were blended with 90 mL of double distilled water for 30 seconds in a Waring blender (Model 33BL79, Waring Prod., New Hartford, Conn.). A fluted filter paper (Whatman #41) was inserted to separate the meat slurry and solution. The pH of the filtered solution was measured using a calibrated pH meter (Model pH meter 125, Corning Science Product, Medfield, Mass.) and recorded as the pH of the meat product.

Measurement of Water Activity

The water activity of samples was measured using a temperature controlled water activity device (AquaLab CX-2, Decagon Device Inc., Pullman, Wash.) in which water activity was computed internally as the ratio of the vapor pressure to the saturation vapor pressure. Samples (5 g) were placed in open-lid plastic cups (diam. 4 cm) and inserted into the device. After equilibration, the water activity and temperature of the sample were displayed and recorded.

Measurement of Moisture Content

Moisture content was determined by the AOAC (AOAC [1997] "Moisture in meat," 950.46, In: *Official methods of analysis*, $16^{th}$ ed., Vol. II, AOAC International, Washington, D.C., pp. 39–1) air oven method. About 4–5 gram samples were weighed into aluminum dishes and dried at 94° C. for seven hours in a convection oven. After removal from the oven, samples were weighed again and the moisture (%) calculated by the following equation:

$$\text{Moisture}(\%) = \frac{\text{Initial sample mass-final sample mass (g)} \times 100}{\text{Initial sample mass (g)}}$$

Research Design and Statistical Analysis

Three replicates of ground beef, ground pork, and breakfast sausage were divided into individual samples. Each replication consisted of a 3×4 factorial arrangement (heat-treated lactic acid treatments—0%, 1%, and 2%; and refrigerated storage times 1, 24, 72 and 168 hours) for individual samples. Each sample was duplicated. All ground beef, ground pork, and sausage data were analyzed separately. Duplicate values were averaged. Data were analyzed as a Randomized Complete Block Design (RCBD) 3×4 factorial arrangement of treatments and times (Cochran, W. G. and Cox, G. M. [1957] *Experimental Designs*, $2^{nd}$ ed., John Wiley & Sons, Inc., New York, N.Y.). Mean differences were ascertained using Fisher's least significant difference (LSD). Polynomial orthogonal contrasts were computed and used for generation of surface response graphs. The probability level was $P \leq 0.05$.

Results

The results indicated that the higher concentration (2%) of heat-treated lactic acid was more bactericidal than either the lower concentration (1%) or water treatments for all ground meats. Heat-treated lactic acid at a concentration of 2% was most effective against *E. coli* O157:H7 populations in the ground meat samples and also maintained the lowest pH over time. Lowering and sustaining pH values to below what is normal for *E. coli* O157:H7 growth provides the stress necessary to produce a reduction in log counts. Both moisture content (percentage) and water activity revealed decreases when heat-treated lactic acid concentration increased and may have provided additional stress to the microorganism.

*E. coli* O157:H7 growth curves

In a nutrient dense medium such as TSB, *E. coli* O157:H7 grows rapidly. The pattern of growth starts with the initial lag phase, followed by an exponential phase, and finally a stationary phase in which cells continue to slightly increase. The death phase is established when growth ceases and certain intrinsic factors such as nutrient content, oxygen, moisture and pH changes inhibit growth (Jay, J. M. [1992] *Modern Food Microbiology*, $4^{th}$ ed., Chapman and Hall, New York, N.Y.).

Inhibition of *E. coil* O157:H7 in ground meat by heat-treated lactic acid

The effect of heat-treated lactic acid as a decontaminant was tested in ground beef, ground pork, and a fresh pork sausage inoculated with *E. coli* O157:H7. Although organic acid solutions of up to 2.5% are allowed by the FSIS of the USDA, a 1% and 2% solution was chosen for this study for surface application which revealed higher concentrations of up to 2% to be more effective.

Inhibition of *Escherichia coli* O157:H7 in ground beef by water and heat-treated lactic acid Of the three treatments, 2% heat-treated lactic acid was the most effective causing a maximum reduction of 2.29 logs of *E. coli* after seven days of refrigerated storage (Table 4). Over the length of the study, 1% heat-treated lactic acid was more effective when compared to the sterile water treatment causing a 0.37 $\log_{10}$ reduction CFU/mL, but not as effective as the 2% treatment. For sterile water-treated or control ground beef, the *E. coli* population grew 0.83 $\log_{10}$ CFU/mL.

Figure 10:
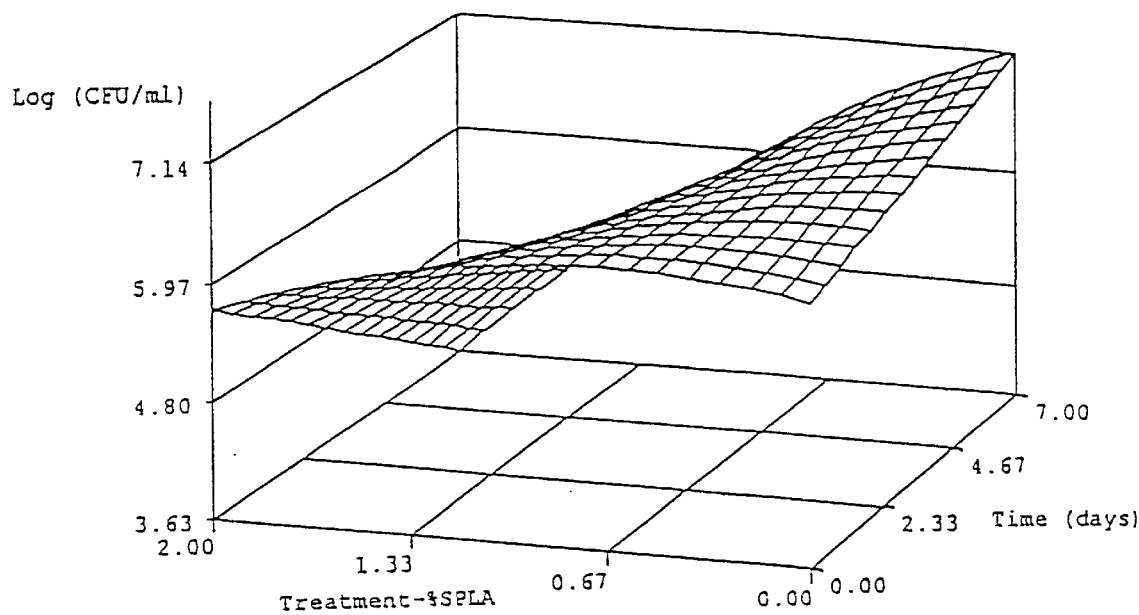
FIG. 10 is a response surface graph of microbial populations of $E.$ $coli$ O157:H7 in ground beef treated with water, 1% heat-treated lactic acid or 2% heat-treated lactic acid solutions.

As treatment concentration of heat-treated lactic acid increased the population of *E. coli* decreased over time (FIG. 10). On the first day of the experiment, at time 0, all three treatments were statistically equal (Table 4). Subsequently, after 1, 3, and 7 days, the means began to separate and on day 7 they were all statistically different from each other. Overall, treatment means with respect to time showed a 1.68 $\log_{10}$ CFU/mL difference between the control samples and 2% heat-treated lactic acid samples in *E. coli* O157:H7 populations.

TABLE 4

Microbial populations of ground beef after treatment with water and heat-treated lactic acid[1]

| Beef | Microbial populations of *E. coli* O157:H7 over time[2] | | | | Overall Treatment Means |
|---|---|---|---|---|---|
| | (0) | (1) | (3) | (7) | |
| Control | 6.39[b] | 6.45[b] | 6.22[b] | 7.22[a] | 6.57 |
| 1% heat-treated lactic acid | 6.28[b] | 6.18[b] | 6.15[b] | 5.91[bc] | 6.13 |
| 2% heat-treated lactic acid | 5.85[bc] | 5.28[cd] | 4.86[d] | 3.56[e] | 4.89 |
| SEM[3] | 0.22 | 0.22 | 0.22 | 0.22 | 0.11 |

[1]Microbial counts expressed as $\log_{10}$ (CFU/mL), time expressed in days, stored at 4° C..
[2]Means with the same letter within a column and row are not significantly different at $P \leq 0.05$, LSD = 0.63.
[3]Pooled standard error of the mean.

Inhibition of *E. coli* O157:H7 in ground pork by water and heat-treated lactic acid

*E. coli* O157:H7 populations in ground pork were lowest in the samples treated with 2% heat-treated lactic acid when compared to the control and 1% heat-treated lactic acid samples. Microbial populations were 2.45 $\log_{10}$ CFU/mL lower after seven days when treated with 2% heat-treated lactic acid (Table 5). Over the length of the study, 1% heat-treated lactic acid was more effective when compared to the sterile water treatment causing a 0.80 $\log_{10}$ reduction CFU/mL, but not as effective as the 2% heat-treated lactic acid treatment. For the sterile water treated ground pork, the *E. coli* population increased by 1.34 $\log_{10}$ CFU/mL.

Figure 11:
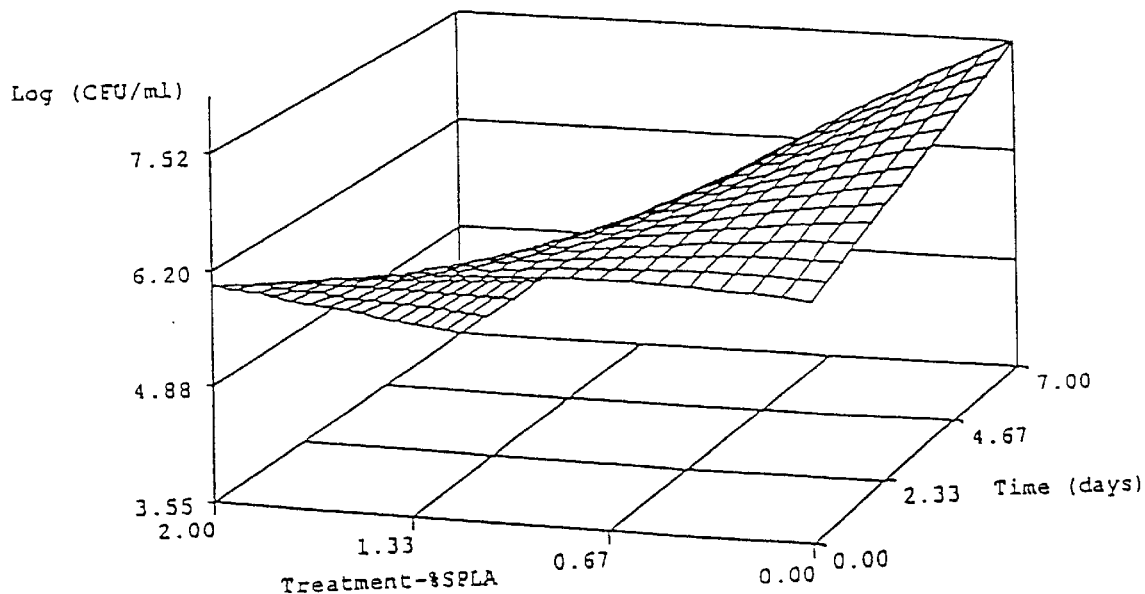
FIG. 11 is a response surface graph of microbial populations of $E.$ $coli$ O157:H7 in ground pork treated with water, 1% heat-treated lactic acid or 2% heat-treated lactic acid solutions.

As treatment concentration of heat-treated lactic acid increased the population of *E. coli* decreased over time (FIG. 11) which is similar to the results attained in the ground beef samples. On the first three days of the experiment, when time equals 0, 1, and 3 days, all three treatments were statistically equal. However, on day 7 the means separated and were all statistically different from each other. Overall treatment means with respect to time show a 1.7 $\log_{10}$ CFU/mL difference between the control treatment and 2% heat-treated lactic acid in *E. coli* O157:H7 populations.

TABLE 5

Microbial populations of *E. coli* O157:H7 over time[2]

| Pork | Microbial populations of *E. coli* O157:H7 over time[2] | | | | Overall Treatment Means |
|---|---|---|---|---|---|
| | (0) | (1) | (3) | (7) | |
| Control | 6.45[b] | 6.42[b] | 6.34[b] | 7.79[a] | 6.75 |
| 1% heat-treated lactic acid | 6.37[b] | 6.31[b] | 6.13[b] | 5.57[b] | 6.10 |
| 2% heat-treated lactic acid | 5.94[b] | 5.42[b] | 5.35[b] | 3.49[c] | 5.05 |
| SEM[3] | 0.44 | 0.44 | 0.44 | 0.44 | 0.22 |

[1]Microbial counts expressed as $\log_{10}$ (CFU/mL), time expressed in days, stored at 4° C.
[2]Means with the same letter within a column and row are not significantly different at $P \leq 0.05$, LSD = 1.29.
[3]Pooled standard error of the mean.

Inhibition of *E. coli* O157:H7 in fresh pork sausage by water and heat-treated lactic acid

*E. coli* O157:H7 populations in fresh pork sausage were lowest in the samples treated with 2% heat-treated lactic acid when compared to the samples treated with sterile water and 1% heat-treated lactic acid. Microbial populations were 1.96 $\log_{10}$ CFU/mL lower after seven days when treated with 2% heat-treated lactic acid and only 0.28 $\log_{10}$ CFU/mL lower for 1% heat-treated lactic acid (Table 6). The control sausage had an overall reduction of *E. coli* population by 1.26 $\log_{10}$ CFU/mL and was the only water treated samples of all three meats that showed a reduction over time.

Figure 12:
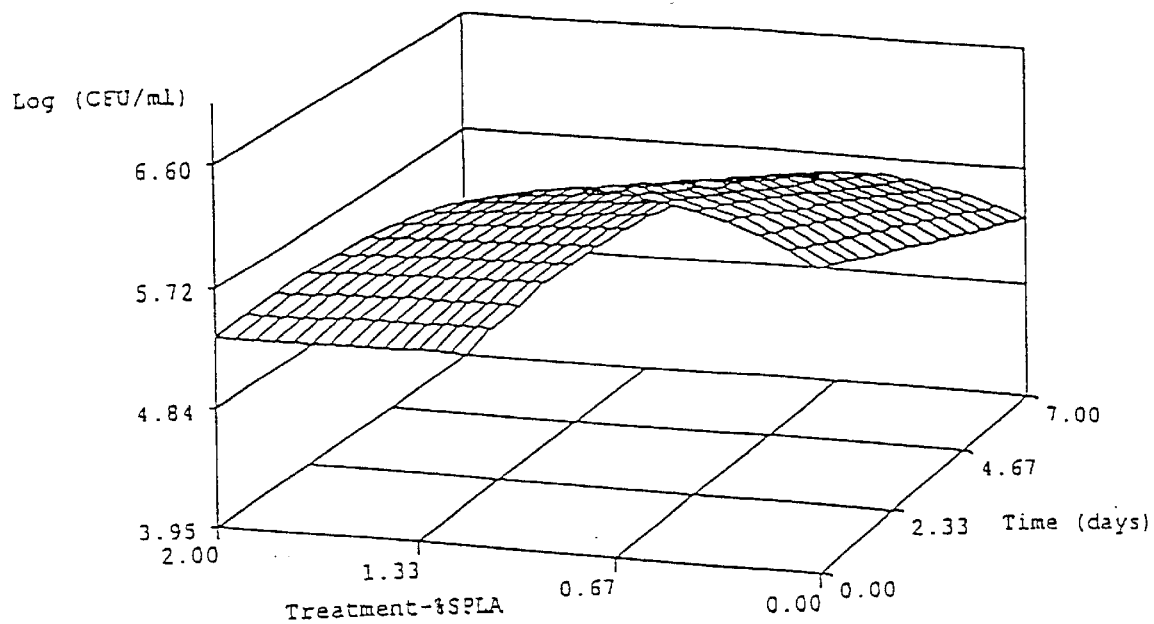
FIG. 12 is a response surface graph of microbial populations of $E.$ $coli$ O157:H7 in fresh pork sausage treated with water, 1% heat-treated lactic acid or 2% heat-treated lactic acid solutions.

Statistically, the interaction between time and treatment was not significant, therefore microbial counts remained consistent over time when considering treatment, especially for 1% heat-treated lactic acid (FIG. 12). Over time, the water and 1% heat-treated lactic acid treated samples were not significantly different from each other but were different from the 2% heat-treated lactic acid treatment. Overall treatment means with respect to time show a 1.32 $\log_{10}$ CFU/mL difference between the water treatment and 2% heat-treated lactic acid in *E. coli* O157:H7 populations.

TABLE 6

Microbial populations of fresh pork sausage after treatment with water and heat-treated lactic acid[1].

| Sausage | Microbial populations of *E. coli* O157:H7 over time | | | | Overall Treatment Means[2] |
|---|---|---|---|---|---|
| | (0) | (1) | (3) | (7) | |
| Control | 6.36 | 6.13 | 5.79 | 5.10 | 6.12[a] |
| 1% heat-treated lactic acid | 6.24 | 6.19 | 6.07 | 5.96 | 5.84[a] |
| 2% heat-treated lactic acid | 5.66 | 5.02 | 4.82 | 3.70 | 4.80[b] |
| SEM[3] | 0.27 | 0.27 | 0.27 | 0.27 | 0.13 |

[1]Microbial counts expressed as $\log_{10}$ (CFU/mL), time expressed in days, stored at 4° C..
[2]Means with the same letter within a column are not significantly different at $P \leq 0.05$, LSD = 0.39.
[3]Pooled standard error of the mean.

pH changes in ground meat

Many parameters determine the survival and growth of microorganisms in food. One effective means of limiting growth is to increase the acidity of a food by creating an unfavorable environment.

pH changes in ground beef

Heat-treated lactic acid treatments had a significant ($P \leq 0.05$) effect on pH in ground beef. The control samples had a significantly higher overall pH at 5.66 (Table 7). These values were consistent with the literature pH values of 5.1 to 6.2 for ground beef (Jay, 1992, supra). The 1% heat-treated lactic acid treated samples resulted in a pH reduction of 1.43 units to 4.23 and the 2% heat-treated lactic acid treated samples reduced the value by 1.74 units to 3.92. The approximate growth range for *Escherichia coli* is 4.4 to 9.0 (Corlett, D. A. and Brown, M. H. [1980] "pH and acidity," In: *Microbial ecology of foods, Vol. 1, Factors affecting the life and death of microorganisms*, 1st ed., J. H. Silliker et al., [ed.] Academic Press, New York, N.Y., pp. 126–135). The addition of both concentrations of heat-treated lactic acid to ground beef changed the pH environment of the meat to at or below the normal range for *Escherichia coli* growth. As concentration of heat-treated lactic acid increased, pH decreased and log reduction (CFU/mL) increased.

Figure 13:
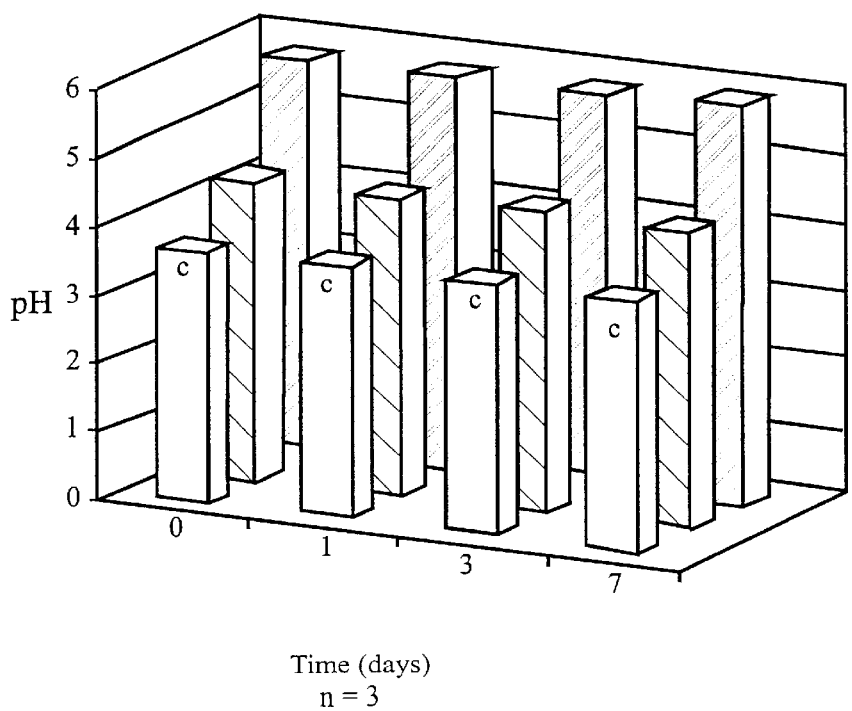
FIG. 13 is a graph showing average pH means of ground beef inoculated with $E.$ $coli$ O157:H7 and treated with either water (black), 1% heat-treated lactic acid (hatched), or 2% heat-treated lactic acid (white) solutions. Bars with different superscripts are significantly different ($P \leq 0.05$).

Statistically, the interaction between treatment and time was non-significant. pH values remained consistent over refrigerated storage time when considering the treatment (FIG. 13). Overall means show that each treatment was significantly different from each other. However, the pH remained constant, and microbial counts increased for control samples and decreased for the heat-treated lactic acid treated samples.

TABLE 7 pH values for ground beef after treatment with water and heat-treated lactic acid[1].

| Beef | pH values over time | | | | Overall pH Means[2] |
|---|---|---|---|---|---|
| | (0) | (1) | (3) | (7) | |
| Control | 5.64 | 5.64 | 5.63 | 5.71 | 5.66[a] |
| 1% heat-treated lactic acid | 4.25 | 4.22 | 4.19 | 4.26 | 4.23[b] |
| 2% heat-treated lactic acid | 3.89 | 3.95 | 3.93 | 3.93 | 3.92[c] |
| SEM[3] | 0.07 | 0.07 | 0.07 | 0.07 | 0.03 |

[1]Time expressed in days, stored at 4° C..
[2]Means with the same letter within a column are not significantly different at P ≦ 0.05, LSD = 0.10.
[3]Pooled standard error of the mean.

pH changes in ground pork

Heat-treated lactic acid treatments in ground pork significantly (P≦0.05) affected the pH values. Control samples had a significantly higher pH value of 5.84 (Table 8). The 1% heat-treated lactic acid treated samples resulted in a pH reduction of 1.62 units to 4.22 and the 2% heat-treated lactic acid treated samples reduced the value by 2.0 units to 3.84.

The approximate pH range of ground pork is 5.3 to 6.9 (Corlett and Brown, 1980, supra).

The interaction between treatment and time was statistically significant (P≦0.05).

Figure 14:
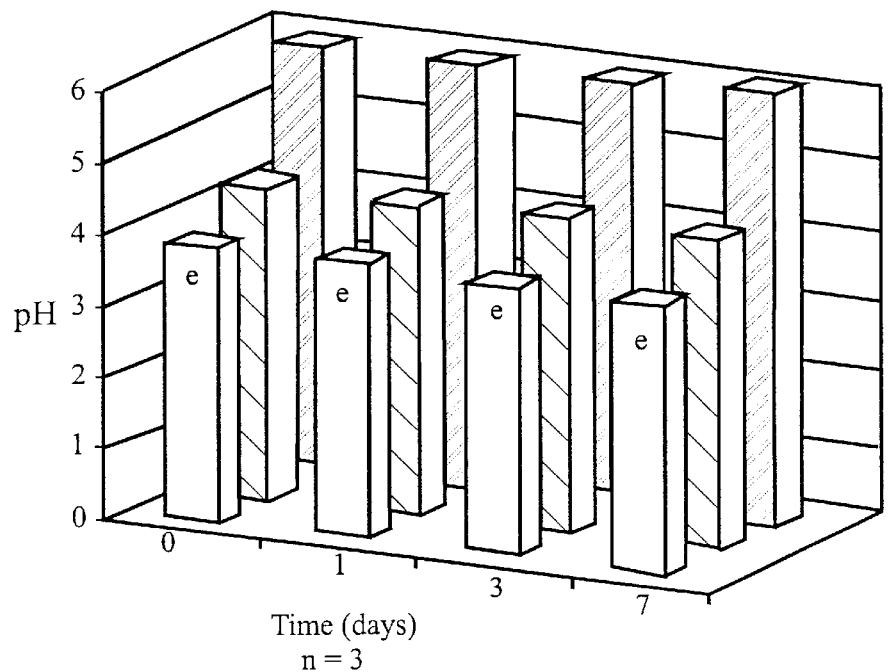
FIG. 14 is a graph showing average pH means of ground pork inoculated with $E.$ $coli$ O157:H7 and treated with either water (black), 1% heat-treated lactic acid (hatched), or 2% heat-treated lactic acid (white) solutions. Bars with different superscripts are significantly different ($P \leq 0.05$).

The pH values of the control samples increased, the 1% heat-treated lactic acid treated samples decreased, and the 2% heat-treated lactic acid treatments remained constant. The differences within treatment are small and this may not be an important difference to observe (FIG. 14).

TABLE 8 pH values for ground pork after treatment with water and heat-treated lactic acid[1].

| Pork | pH values over time[2] | | | | Overall pH Means |
|---|---|---|---|---|---|
| | (0) | (1) | (3) | (7) | |
| Control | 5.80[b] | 5.81[b] | 5.78[b] | 5.97[a] | 5.84 |
| 1% heat-treated lactic acid | 4.29[c] | 4.26[cd] | 4.17[d] | 4.16[d] | 4.22 |
| 2% heat-treated lactic acid | 3.89[e] | 3.84[e] | 3.79[e] | 3.86[e] | 3.84 |
| SEM[3] | 0.04 | 0.04 | 0.04 | 0.04 | 0.02 |

[1]Time expressed in days, stored at 4° C..
[2]Means with the same letter within a column and row are not significantly different at P ≦ 0.05, LSD = 0.11.
[3]Pooled standard error of the mean.

pH changes in fresh pork sausage

Figure 15:
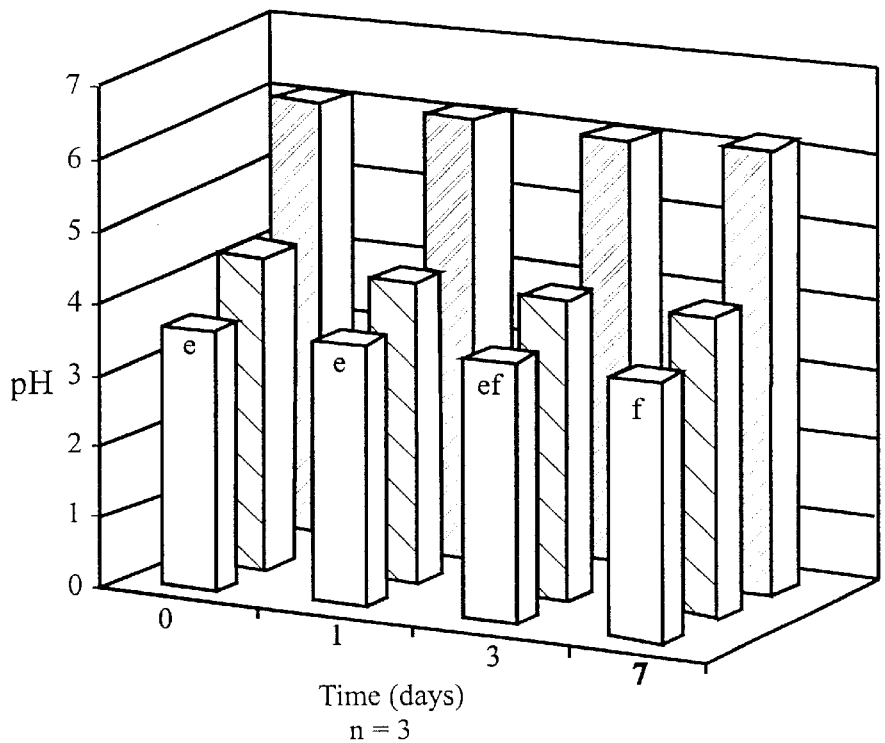
FIG. 15 is a graph showing average pH means of fresh pork sausage inoculated with $E.$ $coli$ O157:H7 and treated with either water (black), 1% heat-treated lactic acid (hatched), or 2% heat-treated lactic acid (white) solutions. Bars with different superscripts are significantly different ($P \leq 0.05$).

The pH values for the sausage samples were significantly (P≦0.05) affected by heat-treated lactic acid treatments (Table 9). The sausage treated with sterile water had the highest overall pH mean of 6.24. The 1% heat-treated lactic acid treated samples resulted in a pH reduction of 1.90 units to 4.34 and the 2% heat-treated lactic acid treated samples reduced the value by 2.41 units to 3.83, which were the largest reductions in pH among the meats tested. The overall means for pH at each treatment were different from each other. There was also a significant (P≦0.05) interaction between treatment and time. The control sample remained constant while the 1% and 2% heat-treated lactic acid treated samples decreased over refrigerated storage time, being significantly different on day 7. The pH range within treatment was statistically significant but very small and essentially not an effective observation (FIG. 15).

Although the control samples had the highest pH values in the experiment, E. coli counts declined by 1.26 logs (Table 9). The microbial counts for each treatment in fresh pork sausage were lower than the corresponding treatments in the ground beef and ground pork. This suggested that the ingredients contained in the formula had impacted microbial growth. When sugar is added to fresh sausage formulas, the natural growth of lactic acid bacteria is induced and will naturally lower the pH of the meat matrix which inhibits microbial growth.

TABLE 9 pH values for fresh pork sausage after treatment with water and heat-treated lactic acid[1].

| Sausage | pH values over time[2] | | | | Overall pH Means |
|---|---|---|---|---|---|
| | (0) | (1) | (3) | (7) | |
| Control | 6.25[a] | 6.22[a] | 6.22[a] | 6.26[a] | 6.24 |
| 1% heat-treated lactic acid | 4.43[b] | 4.37[bc] | 4.34[c] | 4.23[d] | 4.34 |
| 2% heat-treated lactic acid | 3.87[e] | 3.86[e] | 3.82[ef] | 3.75[f] | 3.83 |
| SEM[3] | 0.03 | 0.03 | 0.03 | 0.03 | 0.01 |

[1]Time expressed in days, stored at 4° C..
[2]Means with the same letter within a column and row are not significantly different at P ≦ 0.05, LSD = 0.04.
[3]Pooled standard error of the mean.

Water activity and moisture content of ground meat after treatment

The preservation of foods by drying is a direct consequence of removal or binding of moisture, without which microorganisms do not grow. Lowering the water activity by various means inhibits the growth of microorganisms and influences the rate of enzymatic and chemical changes in foods.

$A_w$ and moisture content of ground beef

No interaction was found between treatment and time for moisture content of ground beef, i.e., moisture was constant for each treatment over time. However, the overall means were significantly different (P≦0.05) with the control samples higher than the 1% and 2% heat-treated lactic acid treated samples, but similar to each other (Table 10). Applying heat-treated lactic acid decreased moisture content, but the difference between treatments was not significant enough to state that one treatment had more of an effect than the other.

There was also no interaction for the water activity values in ground beef. There was a significant difference (P≦0.05) between all treatments, with control having the highest water activity at 0.994, and 2% heat-treated lactic acid with the lowest at 0.987 (Table 11). This indicated that heat-treated lactic acid reduced the initial water activity, but it remained constant over time.

TABLE 10

Moisture values for ground beef after treatment with water and heat-treated lactic acid[1].

| Beef | Moisture values over time[2] | | | | Overall Moisture Means[2] |
|---|---|---|---|---|---|
| | (0) | (1) | (3) | (7) | |
| Control | 50.93 | 51.93 | 52.77 | 51.87 | 51.88[a] |
| 1% heat-treated lactic acid | 47.80 | 51.47 | 41.83 | 51.00 | 50.53[b] |
| 2% heat-treated lactic acid | 50.63 | 50.73 | 50.70 | 49.23 | 50.33[b] |
| SEM[3] | 0.79 | 0.79 | 0.79 | 0.79 | 0.40 |

[1]Time expressed in days, stored at 4° C..
[2]Means with the same letter within a column and row are not significantly different at $P \leq 0.05$, LSD = 1.16.
[3]Pooled standard error of the mean.

TABLE 11

Water activity values for ground beef after treatment with water and heat-treated lactic acid[1].

| Beef | $a_w$ values over time | | | | Overall $a_w$ Means[2] |
|---|---|---|---|---|---|
| | (0) | (1) | (3) | (7) | |
| Control | 0.992 | 0.994 | 0.998 | 0.993 | 0.994[a] |
| 1% heat-treated lactic acid | 0.990 | 0.991 | 0.992 | 0.990 | 0.991[b] |
| 2% heat-treated lactic acid | 0.988 | 0.986 | 0.986 | 0.987 | 0.987[c] |
| SEM[3] | 0.001 | 0.001 | 0.001 | 0.001 | 0.0007 |

[1]Time expressed in days, stored at 4° C..
[2]Means with the same letter within a column and row are not significantly different at $P \leq 0.05$, LSD = 0.0021.
[3]Pooled standard error of the mean.

$A_w$ and moisture content of ground pork

The moisture content for ground pork for the control and 1% heat-treated lactic acid treatments were different over refrigerated storage time while the 2% heat-treated lactic acid treatments remained the same. The significant differences were very small and may not be biologically significant and are relatively constant over time. The overall means were significant with each treatment being different, control had the highest mean of 60.73 and 2% heat-treated lactic acid had the lowest mean of 57.78 (Table 12).

There was no interaction for the water activity value sin ground pork, although there was a significant difference ($P \leq 0.05$) between all treatments with control having the highest water activity at 0.995, and 2% heat-treated lactic acid the lowest at 0.989 (Table 13). This indicated that heat-treated lactic acid reduced the water activity when incorporated but remained constant over time.

TABLE 12

Moisture values for ground pork after treatment with water and heat-treated lactic acid[1].

| Pork | Moisture values over time[2] | | | | Overall Moisture Means |
|---|---|---|---|---|---|
| | (0) | (1) | (3) | (7) | |
| Control | 60.13[c] | 62.07[a] | 60.43[bc] | 60.30[bc] | 60.73 |
| 1% heat-treated lactic acid | 59.73[c] | 58.20[d] | 61.50[ab] | 59.80[c] | 59.81 |
| 2% heat-treated lactic acid | 58.17[d] | 57.90[d] | 57.83[d] | 57.20[d] | 57.78 |
| SEM[3] | 0.47 | 0.47 | 0.47 | 0.47 | 0.23 |

[1]Time expressed in days, stored at 4° C..
[2]Means with the same letter within a column and row are not significantly different at $P \leq 0.05$, LSD = 1.37.
[3]Pooled standard error of the mean.

TABLE 13

Water activity values for ground pork after treatment with water and heat-treated lactic acid[1].

| Pork | $a_w$ values over time | | | | Overall $a_w$ Means[2] |
|---|---|---|---|---|---|
| | (0) | (1) | (3) | (7) | |
| Control | 0.996 | 0.993 | 0.998 | 0.993 | 0.995[a] |
| 1% heat-treated lactic acid | 0.992 | 0.993 | 0.994 | 0.990 | 0.992[b] |
| 2% heat-treated lactic acid | 0.988 | 0.987 | 0.992 | 0.987 | 0.989[c] |
| SEM[3] | 0.001 | 0.001 | 0.001 | 0.001 | 0.0006 |

[1]Time expressed in days, stored at 4° C..
[2]Means with the same letter within a column and row are not significantly different at $P \leq 0.05$, LSD = 0.0019.
[3]Pooled standard error of the mean.

$A_w$ and moisture content of fresh pork sausage

The moisture content for fresh pork sausage for the 1% and 2% heat-treated lactic acid treatments were different over refrigerated storage time while the control treatment remained the same. The significant differences were very small and may not be biologically meaningful and are relatively constant over time. The overall means were significant with each treatment being different, control had the highest mean of 49.25 and 2% heat-treated lactic acid had the lowest mean of 48.79 (Table 14).

There was no interaction for the water activity values in fresh pork sausage between treatment and time. Over time, the water and 1% heat-treated lactic acid treated samples were not significantly different from each other but were different ($P \leq 0.05$) from the 2% heat-treated lactic acid treatment. The control sample had the highest water activity at 0.997 and 2% heat-treated lactic acid the lowest at 0.972 (Table 15). This indicated that heat-treated lactic acid treatments reduce the water activity when applied but remain constant over time. The lower moisture content for fresh pork sausage may be attributed to the ingredients incorporated into the formula as they may affect both microbial counts and pH.

TABLE 14

Moisture values for fresh pork sausage after treatment with water and heat-treated lactic acid[1].

| | Moisture values over time[2] | | | | Overall Moisture |
|---|---|---|---|---|---|
| Sausage | (0) | (1) | (3) | (7) | Means |
| Control | 49.30[b] | 49.27[b] | 42.20[b] | 49.23[b] | 49.25 |
| 1% heat-treated lactic acid | 48.37[bcd] | 48.83[bc] | 49.27[b] | 49.80[b] | 49.07 |
| 2% heat-treated lactic acid | 47.60[cd] | 48.97[bc] | 51.67[a] | 46.93[d] | 48.79 |
| SEM[3] | 0.50 | 0.50 | 0.50 | 0.50 | 0.25 |

[1]Time expressed in days, stored at 4° C..
[2]Means with the same letter within a column and row are not significantly different at $P \leq 0.05$. LSD = 1.45.
[3]Pooled standard error of the mean.

TABLE 15

Water activity values for fresh pork sausage after treatment with water and heat-treated lactic acid[1].

| | $a_w$ values over time | | | | Overall $a_w$ |
|---|---|---|---|---|---|
| Sausage | (0) | (1) | (3) | (7) | Means[2] |
| Control | 0.976 | 0.977 | 0.979 | 0.976 | 0.977[a] |
| 1% heat-treated lactic acid | 0.976 | 0.974 | 0.976 | 0.974 | 0.975[a] |
| 2% heat-treated lactic acid | 0.974 | 0.970 | 0.974 | 0.971 | 0.972[b] |
| SEM[3] | 0.002 | 0.002 | 0.002 | 0.002 | 0.0009 |

[1]Time expressed in days, stored at 4° C..
[2]Means with the same letter within a column and row are not significantly different at $P \leq 0.05$, LSD = 0.0027.
[3]Pooled standard error of the mean.

The approximate minimum $a_w$ value for the growth of *Escherichia coli* is 0.960 (Jay, 1992 supra). This study showed that the bacteria were never stressed past their minimum water requirement; however, in combination with the low pH, the lowered moisture and water activity for ground meats may have contributed to the observed inhibition of *Escherichia coli* O157:H7.

Specific starting compositions and reaction conditions have been described above, and as shown by the above examples and test results, it is possible, with the present invention, to reduce the contamination of a surface, e.g. a food surface such as a freshly-slaughtered animal carcass and of particulate materials such as ground meats. The embodiments described herein are merely exemplary and changes and modifications in the specifically described embodiments can be carried out by one skilled in the art without departing from the scope of the invention. All such changes and modifications are intended to be included within the scope of the invention as defined in the appended claims.

We claim:

1. A method of reducing the microbial contamination of a particulate food material comprising mixing into said food material an effective amount of heat-treated lactic and/or glycolic acid.

2. The method of claim 1 using a heat-treated lactic acid in aqueous solution.

3. The method of claim 2 wherein said solution is less than or equal to a 2% solution.

4. The method of claim 1 wherein said particulate food material is ground meat.

5. The method of claim 4 wherein said ground meat is beef.

6. The method of claim 4 wherein said ground meat is pork.

7. The method of claim 4 wherein heat-treated lactic acid is added to ground meat or sausage in an amount of between about 25 and about 30 mL of a 2% aqueous solution of heat-treated lactic acid per kg of food material.

8. The method of claim 1 wherein said food material is sausage.

9. The method of claim 1 wherein said heat-treated lactic or glycolic acid is added to said food material in an amount sufficient to maintain the pH thereof at less than about 5.0 after about seven days.

10. The method of claim 1 wherein said heat-treated lactic or glycolic acid is added to said food material in an amount sufficient to maintain the pH thereof at less than about 4.0 after about seven days.

11. The method of claim 1 wherein said heat-treated acid is mixed into said food in an aqueous solution of less than or equal to 2.5 weight percent heat-treated acid.

12. A food material comprising heat-treated lactic or glycolic acid mixed therein in an amount effective to maintain the pH of said food material at less than about 5.0 for at least about seven days.

13. The food material of claim 12 comprising ground meat.

14. The food material of claim 13 comprising ground beef.

15. The food material of claim 13 comprising ground pork.

16. The food material of claim 13 comprising sausage.

17. The food material of claim 13 comprising a liquid food material.

18. The food material of claim 13 comprising a gelled food material.

19. The food material of claim 12 wherein heat-treated lactic or glycolic acid is mixed into said food material.

20. The food material of claim 12 wherein heat-treated lactic or glycolic acid is mixed into said food materiel in an amount effective to maintain the pH thereof at less than about 4.0 for at least about seventy-two hours.

21. The food material of claim 12 wherein said heat-treated lactic or glycolic acid is mixed into said food material in a 2% aqueous solution.

22. The food material of claim 12 wherein said heat-treated acid is mixed into said food material in an aqueous solution of less than or equal to 2.5 weight percent aqueous solution.

* * * * *

UNITED STATES PATENT AND TRADEMARK OFFICE
CERTIFICATE OF CORRECTION

PATENT NO. : 6,326,042 B1
DATED : December 4, 2001
INVENTOR(S) : Iannotti et al.

It is certified that error appears in the above-identified patent and that said Letters Patent is hereby corrected as shown below:

Column 3,
Line 21, replace "logo" with -- $\log_{10}$ --.
Line 48, replace "sapra" with -- supra --.

Column 5,
Line 7, replace "method of claim 1" with -- percent of the ester complexes --.

Column 7,
Line 49, 54 and 59, replace "(black)" with -- (double-hatched) --.

Column 8,
Line 4, replace the last "to" with -- per --.

Column 11,
Line 53, replace "beat-treated" with -- heat-treated --.

Column 13,
Line 63, replace "diying" with -- drying --.

Column 15,
Lines 6 and 6, insert -- acid -- between "lactic" and "solution".
Line 25, replace "(MW (0 240)" with -- (MW 240) --.

Column 21,
Line 51, in Table 5, replace "Microbial populations of *E. coli* O157:H7 over time[2]" with -- Microbial populations of ground pork after treatment with water and heat-treated lactic acid[1] --.

UNITED STATES PATENT AND TRADEMARK OFFICE
CERTIFICATE OF CORRECTION

PATENT NO. : 6,326,042 B1
DATED : December 4, 2001
INVENTOR(S) : Iannotti et al.

It is certified that error appears in the above-identified patent and that said Letters Patent is hereby corrected as shown below:

<u>Column 25,</u>
Line 48, replace "value sin" with -- values in --.

Signed and Sealed this

Twenty-third Day of April, 2002

Attest:

JAMES E. ROGAN
*Attesting Officer*     *Director of the United States Patent and Trademark Office*